(12) United States Patent
Jackson et al.

(10) Patent No.: US 7,344,628 B2
(45) Date of Patent: Mar. 18, 2008

(54) CAPILLARY ELECTROPHORESIS-ELECTROCHEMICAL DETECTION MICROCHIP DEVICE AND SUPPORTING CIRCUITS

(75) Inventors: Douglas J. Jackson, New Albany, IN (US); Thomas J. Roussel, Jr., Louisville, KY (US); Mark M. Crain, Georgetown, IN (US); Richard P. Baldwin, Louisville, KY (US); Robert S. Keynton, Louisville, KY (US); John F. Naber, Prospect, KY (US); Kevin M. Walsh, Louisville, KY (US); John. G. Edelen, Versailles, KY (US)

(73) Assignee: The University of Louisville Research Foundation, Louisville, KY (US)

( * ) Notice: Subject to any disclaimer, the term of this patent is extended or adjusted under 35 U.S.C. 154(b) by 341 days.

(21) Appl. No.: 10/364,658

(22) Filed: Feb. 10, 2003

(65) Prior Publication Data

US 2004/0000483 A1    Jan. 1, 2004

Related U.S. Application Data

(60) Provisional application No. 60/355,662, filed on Feb. 8, 2002, provisional application No. 60/355,298, filed on Feb. 8, 2002, provisional application No. 60/355,140, filed on Feb. 8, 2002, provisional application No. 60/355,139, filed on Feb. 8, 2002, provisional application No. 60/355,138, filed on Feb. 8, 2002.

(51) Int. Cl.
*B01D 57/02* (2006.01)
(52) U.S. Cl. ............... 204/451; 204/452; 204/453; 204/601; 204/603; 204/604

(58) Field of Classification Search ........ 204/451–455, 204/601–605
See application file for complete search history.

(56) References Cited

U.S. PATENT DOCUMENTS 5,858,187 A    1/1999    Ramsey et al. ............. 204/452

(Continued)

FOREIGN PATENT DOCUMENTS

DE    19949538    5/2001

(Continued)

OTHER PUBLICATIONS

Seiler et al. (Electroosmotic Pumping and Valveless Control of Fluid Flow within a Manifold of Capillaries on a Glass Chip, Anal. Chem. 1994, 66, 3485-3491).*

(Continued)

*Primary Examiner*—Alex Noguerola
(74) *Attorney, Agent, or Firm*—Greer, Burns & Crain, Ltd.

(57) ABSTRACT

The present invention is a capillary electrophoresis device, comprising a substrate; a first channel in the substrate, and having a buffer arm and a detection arm; a second channel in the substrate intersecting the first channel, and having a sample arm and a waste arm; a buffer reservoir in fluid communication with the buffer arm; a waste reservoir in fluid communication with the waste arm; a sample reservoir in fluid communication with the sample arm; and a detection reservoir in fluid communication with the detection arm. The detection arm and the buffer arm are of substantially equal length.

18 Claims, 13 Drawing Sheets

U.S. PATENT DOCUMENTS

| | | | | |
|---|---|---|---|---|
| 5,932,315 | A | * | 8/1999 | Lum et al. .................. 428/172 |
| 5,942,093 | A | | 8/1999 | Rakestraw et al. ......... 204/450 |
| 6,361,671 | B1 | * | 3/2002 | Mathies et al. ............ 204/452 |
| 6,685,809 | B1 | * | 2/2004 | Jacobson et al. ........... 204/450 |

FOREIGN PATENT DOCUMENTS

| | | |
|---|---|---|
| GB | 2302590 | 1/1997 |
| WO | WO96/04547 | 2/1996 |
| WO | WO97/36170 | 10/1997 |
| WO | WO98/09161 | 3/1998 |
| WO | WO00/77509 | 12/2000 |
| WO | WO01/51918 | 7/2001 |

OTHER PUBLICATIONS

Conkin, J., M. Crain, R. Pai, M. Martin, et al., "Alternative Fabrication Methods for Capillary Electrophoretic Device Manufacturing," printed from http://meccca.spd.louisville.edu/~lab-on-a-chip/xyz_pubs.htm, Louisville, KY: University of Louisville (2001).

Pai, R., T. Roussel, Jr., M. Crain, D. Jackson, et al., "Integrated Electrochemical Detection for Lab on a Chip Analytical Microsystems," printed from http://mecca.spd.lousville.edu/~lab-on-a-chip/xyz_pubs.htm, Louisville, KY: University of Louisville (2001).

T. Roussel, "A Capillary electrophoresis platform with "on-chip" electrochemical detection: experimental and computational flow studies", 2001, Micro-Electromechanical Systems, vol. 3, pp. 781-785.

K. Seiler, et al., "Planar glass chips for capillary electrophoresis: repetitive sample injection, quantification, and separation efficiency", May 15, 1993, Analytical Chemistry, American Chemical Society, Columbus, US, vol. 65 No. 10, pp. 1481-1488.

* cited by examiner

US 7,344,628 B2

CAPILLARY ELECTROPHORESIS-ELECTROCHEMICAL DETECTION MICROCHIP DEVICE AND SUPPORTING CIRCUITS

RELATED APPLICATIONS

This non-provisional application is based on Provisional Applications Ser. No. 60/355,662, filed Feb. 8, 2002; Ser. No. 60/355,298, filed Feb. 8, 2002; Ser. No. 60/355,140, filed Feb. 8, 2002; Ser. No. 60/355,139, filed Feb. 8, 2002; and Ser. No. 60/355,138, filed Feb. 8, 2002.

FEDERALLY SPONSORED RESEARCH OR DEVELOPMENT

The subject matter of this application may in part have been funded by National Science Foundation XYZ Lab-on-a-chip Grant # 9980831 and Department of Energy Grant # 4-64111-01. The government may have certain rights in this invention.

BACKGROUND

Electrophoresis is the migration of charged electrical species dissolved in an electrolyte solution in response to an applied electric field. Cations (positively charged species) migrate toward the negatively charged cathode and anions (negatively charged species) are attracted toward the positively charged electrode or anode. Capillary electrophoresis (CE) utilizes high voltages across buffer filled capillaries to achieve separation of substances based on the relative charge, and to a smaller extent the size.

The operation of a typical CE system involves the application of a high voltage across capillaries that have been filled with an electrolyte solution that conducts current through the inside of the capillaries. The ends of the capillaries are dipped into reservoirs filled with the electrolyte solution. The reservoirs are usually glass containers that hold a large volume of electrolyte. Electrodes made of an inert material such as platinum are also inserted into the electrolyte reservoirs to complete the electrical circuit. A small volume of a sample is injected into one end of the capillary by applying a voltage across the capillary to induce flow in the buffer solution. The capillary passes through a detector, usually an ultraviolet (UV) absorbance detector, at the end of the capillary that is opposite from the injection end. Application of the voltage once again causes the movement of sample ions in an electroendosmotic flow (EOF) or in a plug-like flow, towards the detection end of the capillary, and allows the separation of positive, neutral, and negatively charged sample ions.

Initial CE systems were bulky, heavy and not easily transported from place to place. These systems required large sample sizes of sometimes expensive substances. Furthermore, a relatively simple, easy method of fabricating these systems does not exist. Therefore, there has been a need to shrink the entire capillary electrophoresis system to a microfabricated microchip capillary system and create a portable analytical instrument ("lab-on-a-chip").

Attempts at developing integrated CE systems using standard microfabrication techniques have been made. However, these systems have generally included laser-induced florescence detection methods that are implemented with components that are by necessity off-chip and therefore separated from the substrate containing the separation components, and hence not truly integrated.

It is therefore an object of this invention to provide a fully-integrated electrochemical detection system and method for manufacturing such a device.

BRIEF SUMMARY OF THE INVENTION

In a first aspect, the present invention is a capillary electrophoresis device, comprising a substrate; a first channel in the substrate, and having a buffer arm and a detection arm; a second channel in the substrate intersecting the first channel, and having a sample arm and a waste arm; a buffer reservoir in fluid communication with the buffer arm; a waste reservoir in fluid communication with the waste arm; a sample reservoir in fluid communication with the sample arm; and a detection reservoir in fluid communication with the detection arm. The detection arm and the buffer arm are of substantially equal length.

In a second aspect, the present invention is a capillary electrophoresis device, comprising a substrate; a first channel in the substrate, and having a buffer arm and a detection arm; a second channel in the substrate intersecting the first channel, and having a sample arm and a waste arm; a buffer reservoir in fluid communication with the buffer arm; a waste reservoir in fluid communication with the waste arm; a sample reservoir in fluid communication with the sample arm; and a detection reservoir in fluid communication with the detection arm. The detection arm and the buffer arm have a balanced flow rate upon application of a first voltage to the buffer reservoir, the detection reservoir, and the sample reservoir; and a second voltage to the waste reservoir.

In a third aspect, the present invention is a method for performing capillary electrophoresis comprising providing a substrate having:
  a first channel having a buffer arm and a detection arm;
  a second channel intersecting the first channel and having a sample arm and a waste arm;
  a sample reservoir for receiving a sample in fluid communication with the sample arm;
  a buffer reservoir in fluid communication with the buffer arm;
  a waste reservoir in fluid communication with the waste arm;
  a detection reservoir in fluid communication with the detection arm. The first and second channels are filled with an electrolyte solution; applying voltages to the buffer, sample, and detection reservoirs to cause the electrolyte solution in the buffer arm, the sample arm, and the detection arm to flow towards the waste reservoir to form a pinched plug; and flowing the pinched plug along the detection arm to the detection reservoir.

In a fourth aspect, the present invention is a method for manufacturing a capillary electrophoresis device comprising forming, in a first substrate:
  a first channel having a buffer arm and a detection arm;
  a second channel intersecting the first channel and having a sample arm and a waste arm,
  a sample reservoir for receiving a sample in fluid communication with the sample arm,
  a buffer reservoir in fluid communication with the buffer arm,;
  a waste reservoir in fluid communication with the waste arm; and
  a detection reservoir in fluid communication with the detection arm;

forming, in a second substrate:
  a waste reservoir electrode;
  a sample reservoir electrode;

a buffer reservoir electrode; and at least three detection reservoir electrodes;

aligning the first substrate with the second substrate; and bonding the first substrate to the second substrate.

In a fifth aspect, the present invention is a capillary electrophoresis device, comprising a capillary channel; a detection reservoir in fluid communication with the capillary channel; a CE-Aux electrode in the detection reservoir; a reference electrode in the detection reservoir, and; a work electrode in the detection reservoir.

In a sixth aspect, the present invention is a capillary electrophoresis device, comprising a substrate; a first channel in the substrate, and having a buffer arm and a detection arm; a second channel in the substrate intersecting the first channel, and having a sample arm and a waste arm; a buffer reservoir in fluid communication with the buffer arm; a waste reservoir in fluid communication with the waste arm; a sample reservoir in fluid communication with the sample arm; a detection reservoir in fluid communication with the detection arm; the detection reservoir having three electrodes; and three electrodes in the detection reservoir.

In a seventh aspect, the present invention is a power supply for a capillary electrophoresis device, comprising means for providing a reference voltage; means for converting the reference voltage to a positive voltage output; means for converting the reference voltage to a negative voltage output; means for connecting a rail voltage supply to a battery;

In an eighth aspect, the present invention is a power supply for a capillary electrophoresis device, comprising a DC voltage source to supply a reference voltage; a positive voltage circuit to convert the reference input voltage to a positive voltage output; a negative voltage circuit to convert the reference input voltage to a negative voltage output; and a rail voltage supply coupled to the positive voltage circuit and the negative voltage circuit, and configured to receive a voltage supplied by a battery.

In a ninth aspect, the present invention is an interface circuit for a capillary electrophoresis device having a plurality of reservoirs and a plurality of capillary channels, comprising a first voltage supply; a second voltage supply; a first switch connected to the first voltage supply and a first one of the plurality of reservoirs; a second switch connected to the second voltage supply and a second one of the plurality of reservoirs; and a controller connected to the first switch and the second switch.

DETAILED DESCRIPTION

The present invention described herein with references to the drawings, wherein like components are identified with the same references. The descriptions of the embodiments contained herein are intended to be exemplary in nature and are not intended to limit the scope of the invention, which is defined in the claims herein.

Figure 1:
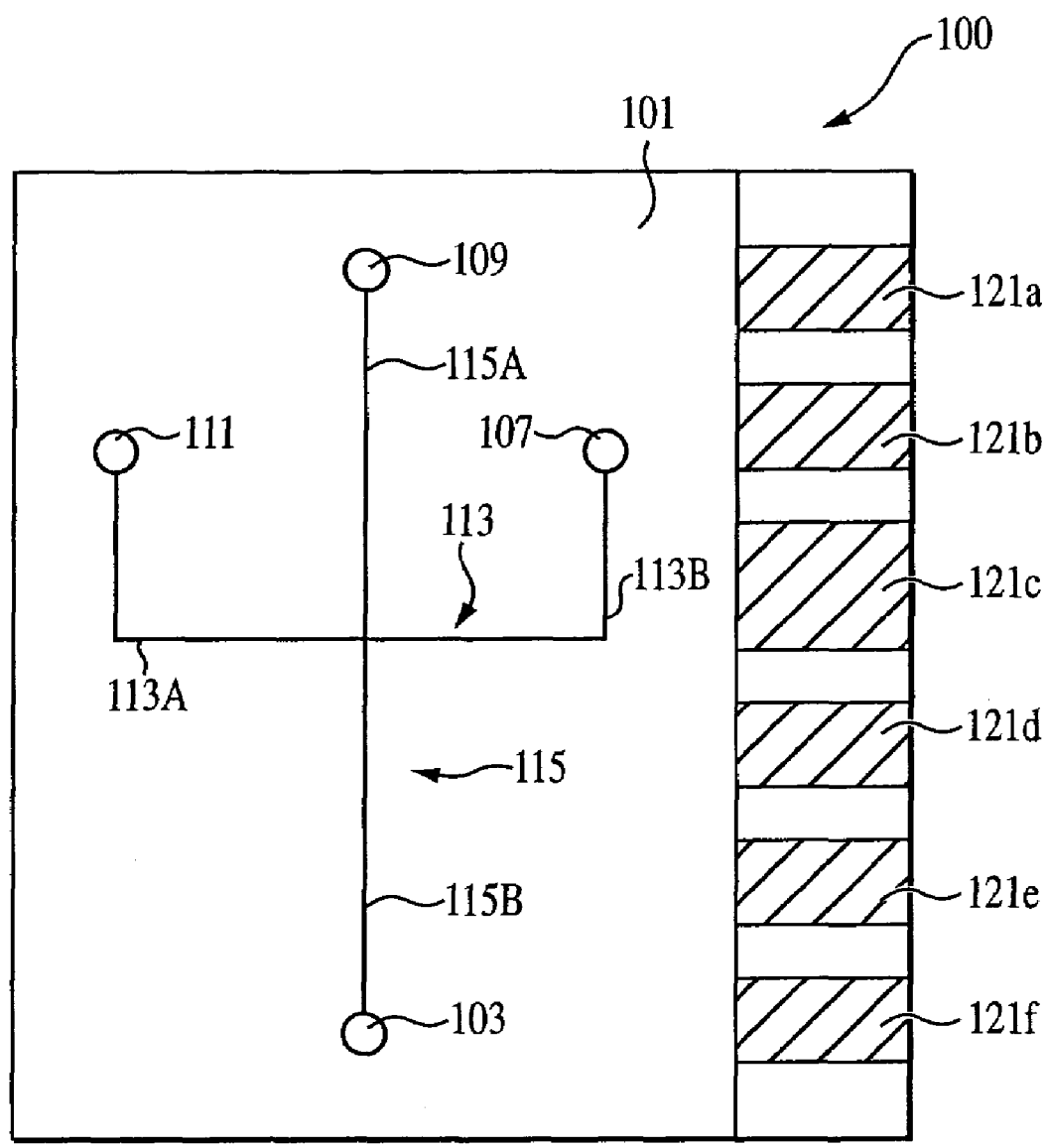
FIG. 1 shows one embodiment of a balanced geometry capillary electrophoresis (CE) microchip device.

FIG. 1 shows one embodiment of a balanced geometry capillary electrophoresis (CE) microchip device 100. The CE microchip device 100 includes a substrate 101, a detection reservoir 103, electrodes 121a-f, a sample reservoir 107, a buffer reservoir 109, a waste reservoir 111 and a plurality of capillary channels 113 and 115.

The sample reservoir 107 is utilized to receive a sample substance (also referred to herein as "analyte"), for eventual detection by CE microchip device 100. The detection reservoir 103 is utilized to receive the analyte sample, as well as house the electrochemical detection cell electrodes. The buffer reservoir 109 is utilized as a support reservoir that contains excess fresh buffer solution. The waste reservoir 111 is utilized to collect excess samples during the injection mode and also provides an electrical connection for the driving electronics. In addition, the waste reservoir 111 accepts fluid flow in the detection and injection modes.

Capillary channel 113 (also referred to herein as a "sample capillary channel) connects the waste reservoir 111 to the sample reservoir 107 and capillary channel 115 (also referred to herein as the "separation capillary channel") connects the buffer reservoir 109 to the detection reservoir 113. The capillary channels 113 and 115 are preferably filled with an electrolyte solution, or buffer, that conducts current through the inside of the channels. However, other types of solutions may also be used without departing from the scope of the present invention. Additionally, the capillaries may be chemically treated to enhance particular separation techniques or decrease time for analysis;

In one embodiment, capillary channels 113 and 115 are each comprised of two arms. Specifically, as shown in FIG. 1, sample capillary channel 113 is comprised of a waste arm 113A that is in fluid communication with the waste reservoir and a sample arm 113B that is in fluid communication with the sample reservoir. Similarly, separation capillary channel 115 is comprised of a buffer arm 115A that is in fluid communication with the buffer reservoir and a detection arm 115B that is in fluid communication with the detection reservoir. As shown in FIG. 1, arms 113A and 113B may be bent for convenience, thus reducing the size of the CE device 100.

In addition, arms 115A and 115B are preferably designed such that the flow rates throughout the arms 115A and 115B are balanced. A "balanced" flow rates means that a pinched plug is formed in the intersection of the sample and separation capillary channels when the detection and buffer reservoirs are held at equal potential and a voltage is applied to the waste reservoir. For example, the flow rates in capillary arms 115A and 115B may be within 10% of each other. A "pinched plug" means that the sample that flows into the intersection of the capillary channels kept within the intersection by the flow of fluid from the detection arm 115A and the buffer arm 115B, i.e. no sample leaks into the detection or buffer arms during injection In one approach, arms 115A and 115B may be substantially equal in length and may have a length of 0.25 centimeters to 10 centimeters. For the purposes of this description, "substantially equal in length" means that, when a voltage is applied to the waste reservoir and the two ends of the separation capillary channel are kept at an equal potential, the flow rate through the arms 115A and 115B will be balanced. However, the flow rates may also be balanced in capillary arms having different lengths by adjusting the cross-sectional geometry of the capillaries.

Fabrication of CE Microchip Device

Figure 2:
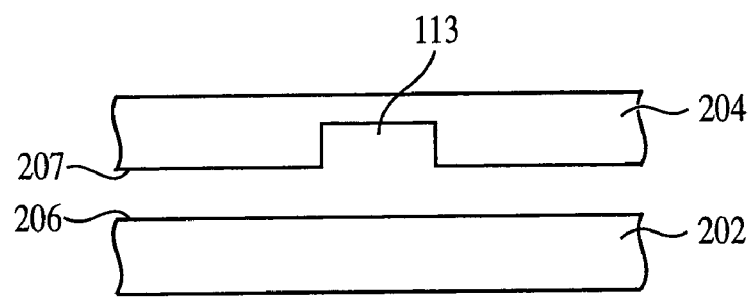
FIG. 2 shows a cross-sectional view of a portion of the first and second substrates according to the present invention.

In one embodiment, the CE microchip device 100 is fabricated using a first substrate 202 and a second substrate 204 (see FIG. 2). The first and second substrates are preferably glass substrates and may be pre-coated with a photoresist and/or metal, such as ultra-flat soda lime glass photomask blanks. Alternatively, the substrates may be of any suitable material without the photoresist and metal layers. If the substrates do not include these layers, the photoresist and metal layers may be added at the beginning of fabricating the CE microchip device.

Figure 3:
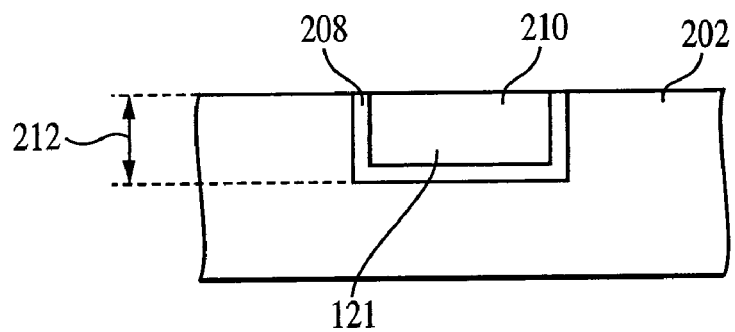
FIG. 3 shows a cross-sectional view of an electrode according to the present invention.

The first substrate 202 may includes a plurality of electrodes 121a-f. FIG. 3 shows one example of an electrode 121 that is recessed into the first substrate 202 and that is approximately flush with a surface 206 of the substrate. The electrodes are preferably plated with an adhesion layer 208 and a metallization layer 210. However, the electrodes may also include be composed of materials such as, carbon, silver-silver chloride or copper. In one example, the depth 212 of the recessed electrode 121a-f is approximately 0.3 µm, the adhesion layer 208 is a layer of titanium approximately 10 nm thick and the metallization layer 210 is a layer of platinum approximately 300 nm thick.

The second substrate 204 includes the capillary channels 113 and 115 (a cross-section of one example capillary channel is shown in FIG. 2), the detection reservoir 103, the sample reservoir 107, the buffer reservoir 109, and the waste reservoir 111. The reservoirs may be formed as apertures that extend through the second substrate 204. It should be noted that a varying configuration of reservoirs and capillary channels may be utilized without departing from the present invention.

Figure 4A:
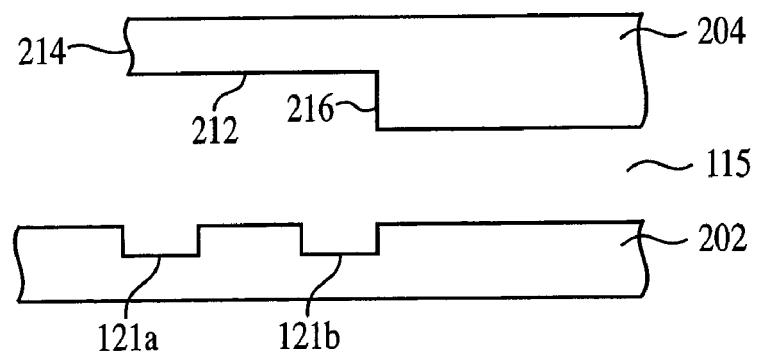
FIG. 4A shows a cross-sectional view of one embodiment of a detection reservoir according to the present invention.

FIG. 4A shows one embodiment of the detection reservoir 103. To aid in containing the substance being detected (the plug) at the detection reservoir 103, a shelf 212 is included in the second substrate 204. The thickness of the shelf "t" equal to the depth of the separation capillary 115. However, in one embodiment, the shelf may have a thickness "t" of one-half that of the top substrate 204. In addition, two electrodes 121a, 121b, or their associated interconnect lines are located under the shelf 212 and in the first substrate 202. In one embodiment, electrode 121a may be located approximately under a first edge 214 of the shelf 212. Electrode 121b may then also be located approximately under a second edge 214 of the shelf 212. However, electrode 121b may also be positioned closer to electrode 121a.

Figure 4B:
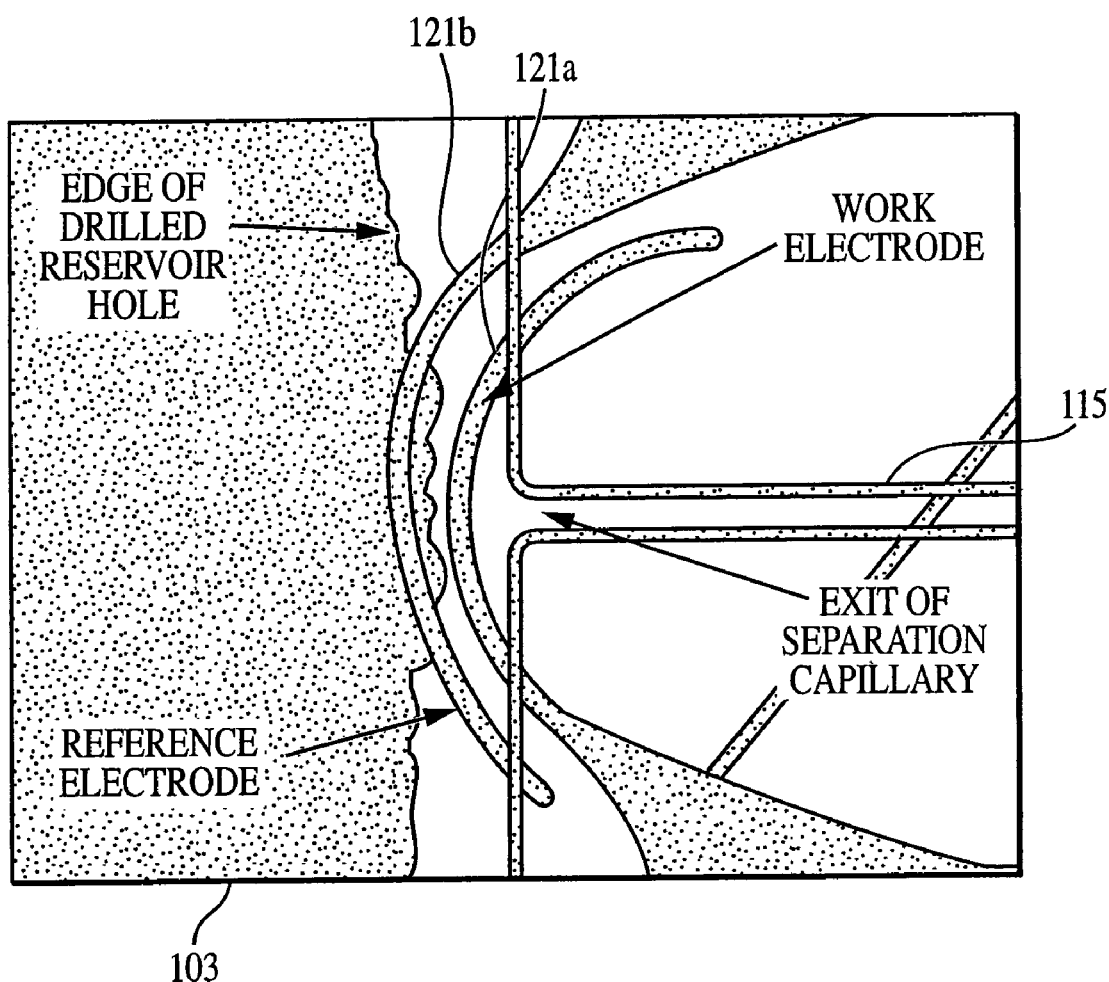
FIG. 4B shows a top view of one embodiment of a detection reservoir according to the present invention.

FIG. 4B shows a top view of one exemplary embodiment of the detection reservoir. In this embodiment, the electrode widths are approximately 40 um, the distance between the electrodes 121a and 121b is approximately 150 um and the separation capillary width is approximately 50 um.

In one embodiment, the waste reservoir 111, the buffer reservoir, 109 and the sample reservoir 107 may each also include a shelf as described above for the detection reservoir. In this embodiment, an electrode located in waste, buffer, and sample reservoirs would also preferably be located under the associated shelf. However, it is noted that the waste, buffer, and sample reservoirs may alternatively be constructed without a shelf whereby the associated electrode may be positioned within the reservoir, at the intersection of the capillary and the reservoir, or in any other suitable location.

Figure 5:
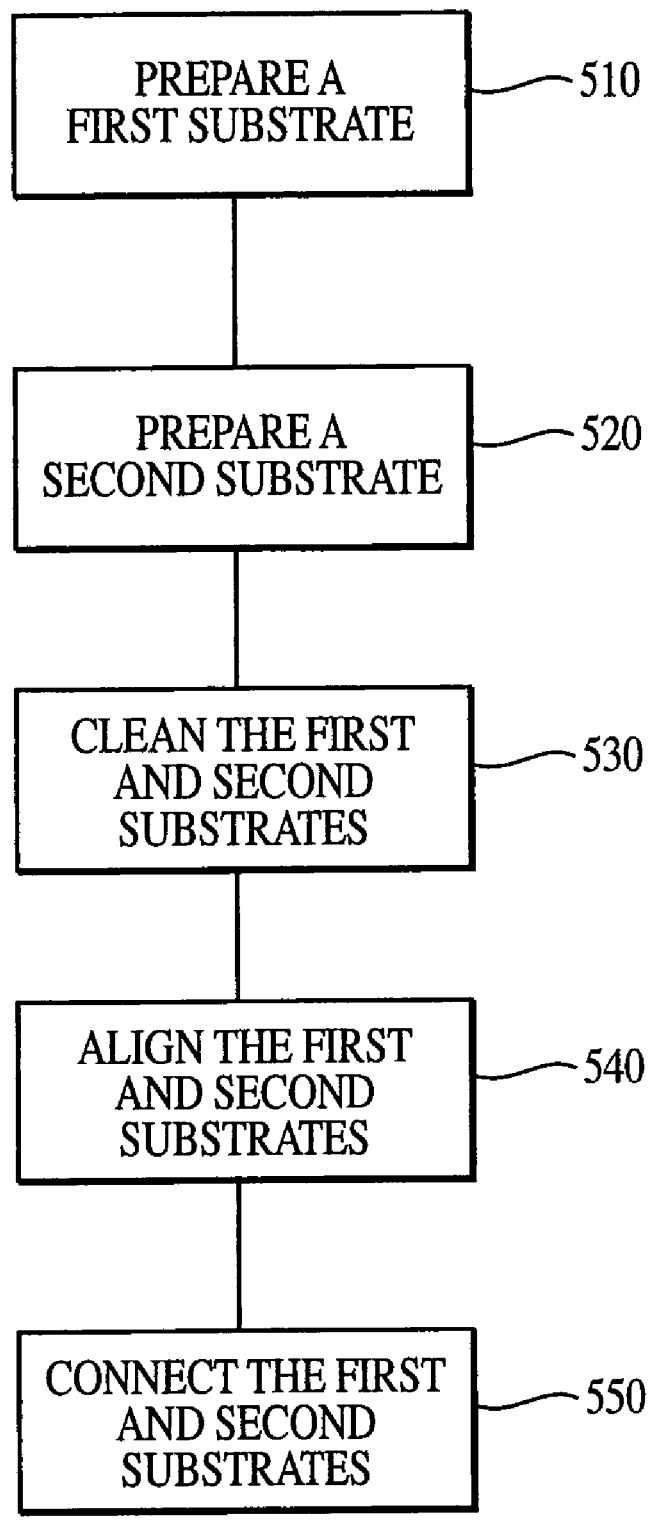
FIG. 5 shows a flow-chart illustrating the basic steps involved in fabricating a microfabricated capillary electrophoresis device according to the present invention.

FIG. 5 shows a flow chart depicting the general process for manufacturing the CE microchip device 100. Steps 510 and 520 involve preparing the first and second substrates. As noted above, the substrates may be glass, such as a soda lime glass, or any other suitable substrate material. One example of a suitable substrate is the ultra-flat soda lime photomask blank manufactured by Nanofilm, Inc., Westlake Village, Calif., which includes a thin layer of chrome and a layer of positive photoresist (in particular, AZS 1518 positive photoresist). If the substrate being used is not pre-coated with a metallization and a photoresist layer, Steps 510 and 520 may also include coating the substrate with a metallization layer and a photoresist layer.

Figure 6:
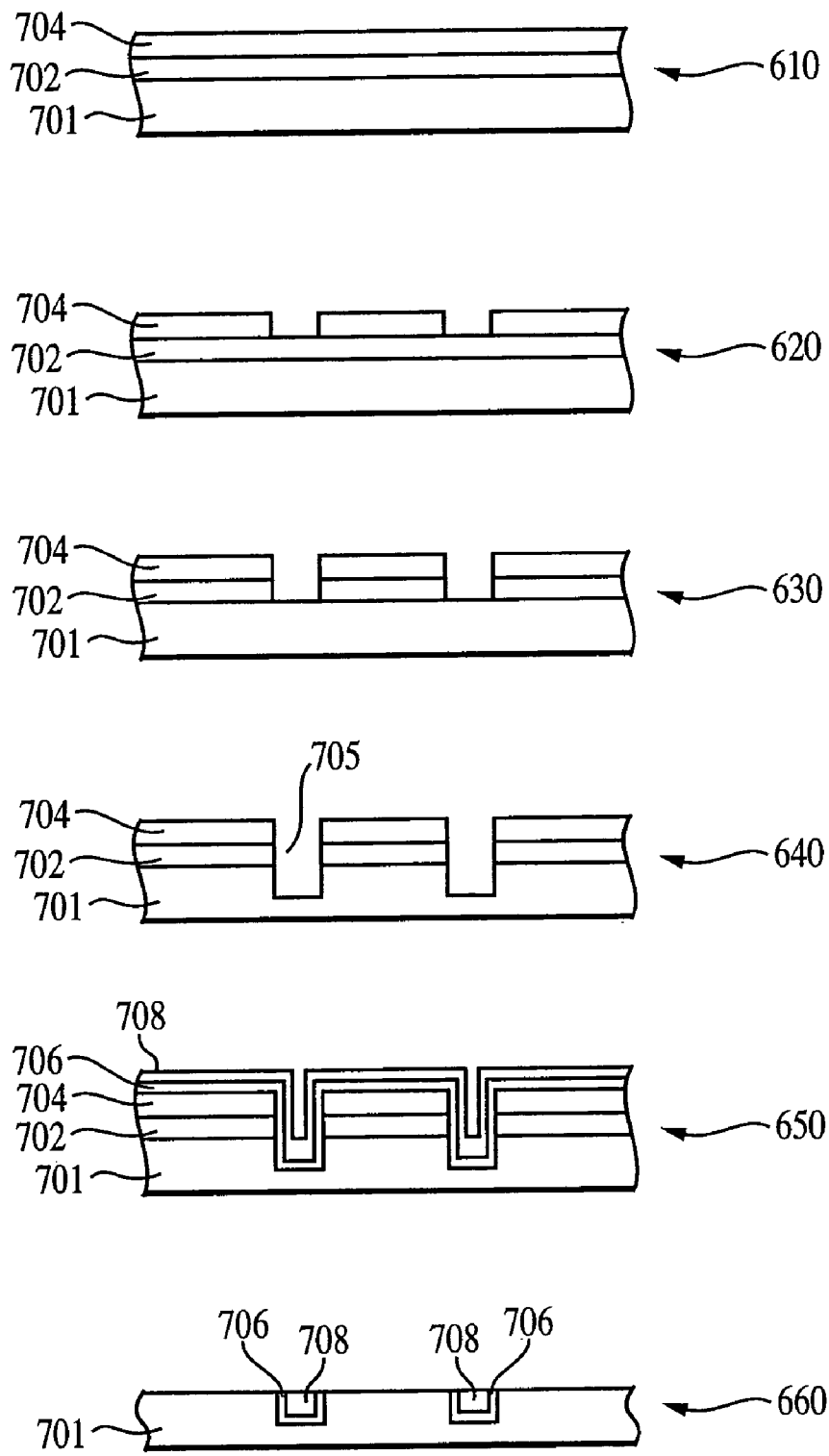
FIG. 6 illustrates the fabrication steps involved in preparing the first substrate according to the present invention.

Preparing the first substrate in Step 510 includes forming the electrodes 121a-f in the first substrate 202. One exemplary process for forming the electrodes 121a-f is illustrated in FIG. 6. It should be noted that the steps described in FIG. 6 are utilized with a pre-coated substrate that includes a thin layer of chrome and a positive photoresist layer. It will be obvious to one skilled in the art that the process may include different steps depending on the composition of the first substrate and the type of photoresist used.

Step 610 illustrates the starting point of the bottom substrate which includes a substrate 701, a chrome layer 702 and a photoresist layer 704. In step 620, a darkfield photomask (not shown) that includes an inverse pattern of the desired electrodes and their interconnect lines is prepared, and the inverse pattern is then transferred to the photoresist layer 704 using known techniques. In step 630, the chrome layer 702 that is not covered by the photoresist layer is etched for a time sufficient to expose the substrate 701. In one embodiment, the chrome is etched using a chrome etchant such as CEP-200 Micro Chrome etchent. As shown in step 630, the substrate 701 is only exposed in the regions not covered by the photoresist 704.

In step 640, the substrate 701 is then etched to form recessed electrode areas 705. This step is performed in order to keep the substrate 701 as flat as possible. In the present embodiment, the substrate 701 is etched for approximately 30 seconds at room temperature in an approximately 6:1 Buffered Oxide Etch (BOE, J. T. Baker, Phillipsburg, N.J.) to form recessed electrode areas 705 having a depth of approximately 0.3 pm. Of course, if different substrate materials are used, they may require different etches or other methods of removal and different exposure times and conditions.

In step 650, the electrode material is deposited. The electrode material is generally comprised of an adhesion layer 706 and a metallization layer 708. In one embodiment, the adhesion layer 706 is a layer of titanium with a thickness of approximately 10 nm and the metallization layer 708 is a layer of platinum with a thickness of 300 nm. Preferably, the titanium and platinum layers are sputtered onto the substrate 701. However, other techniques may also be used to deposit the adhesion and metallization layers.

In step 660, the formation of the recessed electrodes 709 is completed using a lift-off process. The substrate 701 is soaked in a dissolving solution, such as acetone, to dissolve the positive photoresist. As a result, the photoresist layer 704, as well as the titanium 706 and platinum 708 layers above the photoresist layer are removed, while the titanium 706 and platinum 708 layers in the recessed electrode areas remain to form the recessed electrodes 709. The chrome layer 702 is then etched away using methods known in the art. It is noted that if a different photoresist is used, a different dissolving solution may need to be used. For example, a wet etching process may be used. However, the wet etching process would require multiple steps, whereas the lift-off process described above allows both layers of the electrodes to be removed in a single step.

Returning to FIG. 5, preparing the second substrate in Step 520 include forming the capillary channels and the reservoir openings. In one embodiment, pre-coated photomask blanks, which include a thin layer of chrome and a layer of positive photoresist are used. The capillary channels are photolithographically patterned and wet-etched in an approximately 6:1 BOE at room temperature for approximately 30 minutes at an average etch rate of approximately 0.66 μm/minute, resulting in capillary channels with an average width of approximately 50 μm (approximately 60 μm at the surface of the substrate and approximately 40 μm at the bottom of the capillary channels). This etch rate produces a channel that is approximately 25 μm deep. The remaining photoresist and chrome is then removed. It is noted that if a different substrate is used, the etch conditions may need to be adjusted. Additionally, other methods may also be used to form the capillary channel, such as micromachining.

The reservoirs 103, 107, 109, and 111 are preferably formed by drilling the substrate with a diamond core drill bit. In one embodiment, another may also be drilled approximately 1 radius away from the center of the detection reservoir to create space for the electrochemical detection cell. Other suitable methods of forming the reservoir openings may also be used depending on the type of substrate being used.

In Step 530, the first and second substrates are cleaned. In one embodiment, the substrates are cleaned using a conventional RCA base cleaning procedure. However, the top and bottom substrates may be cleaned using any other appropriate cleaning procedure such as a piranha dip (sulfuric acid and hydrogen peroxide). In one approach, the first substrate is cleaned for approximately 30 seconds and the second substrate is cleaned for approximately 10 minutes. The first and second substrates are then soaked in deionized water for approximately 2 minutes.

In Step 540 the first and second substrates are aligned. Aligning the substrates generally involves a two step process—a preliminary alignment and a final alignment. The first and second substrates are preliminarily aligned by bringing together the inner surfaces 206, 207 of each substrate, thereby forming an interface between the two substrates. In one embodiment, the substrates may be brought together under running water. The outer surfaces of the substrates are then dried, preferably by blowing the outer surfaces dry with clean nitrogen.

The final alignment is then performed by sliding the substrates along the interface formed by the two substrates until the desired alignment is obtained. Preferably, the substrates are aligned so that each of the CE electrodes 121c-e, or their interconnect lines, is positioned within a respective on of the waste, sample, and buffer reservoirs. Additionally, the substrates are also preferably aligned so that electrodes 121a, 121b are located under the shelf 212 of the detection reservoir 103 and close to the end of the separation capillary 115 as shown in FIG. 4A. An optical microscope or other magnifying device can be used to aid in this process.

Step 650 includes physically connecting the first and second substrates together. In one embodiment, connecting the substrates includes applying pressure and heat to the substrates. A weight is first placed on the substrates to produce a pressure of approximately 50 g/cm2. The substrates under pressure are then thermally bonded together at 625° C. The substrates and the weight are then placed between two Alumina blocks and subjected to a bonding sequence involving a 3° C./minute ramp up of temperature to 626° C., followed by a 30 minute soak in air and then a 3° C./minute ramp down of temperature to a minimum of 100° C. Careful ramping of the temperature is required if glass substrates are used to prevent the substrates from fracturing due to induced thermal stress. If other substrate materials are used, different bonding methods or other connecting procedures may be used.

Interface Circuit

Figure 7:
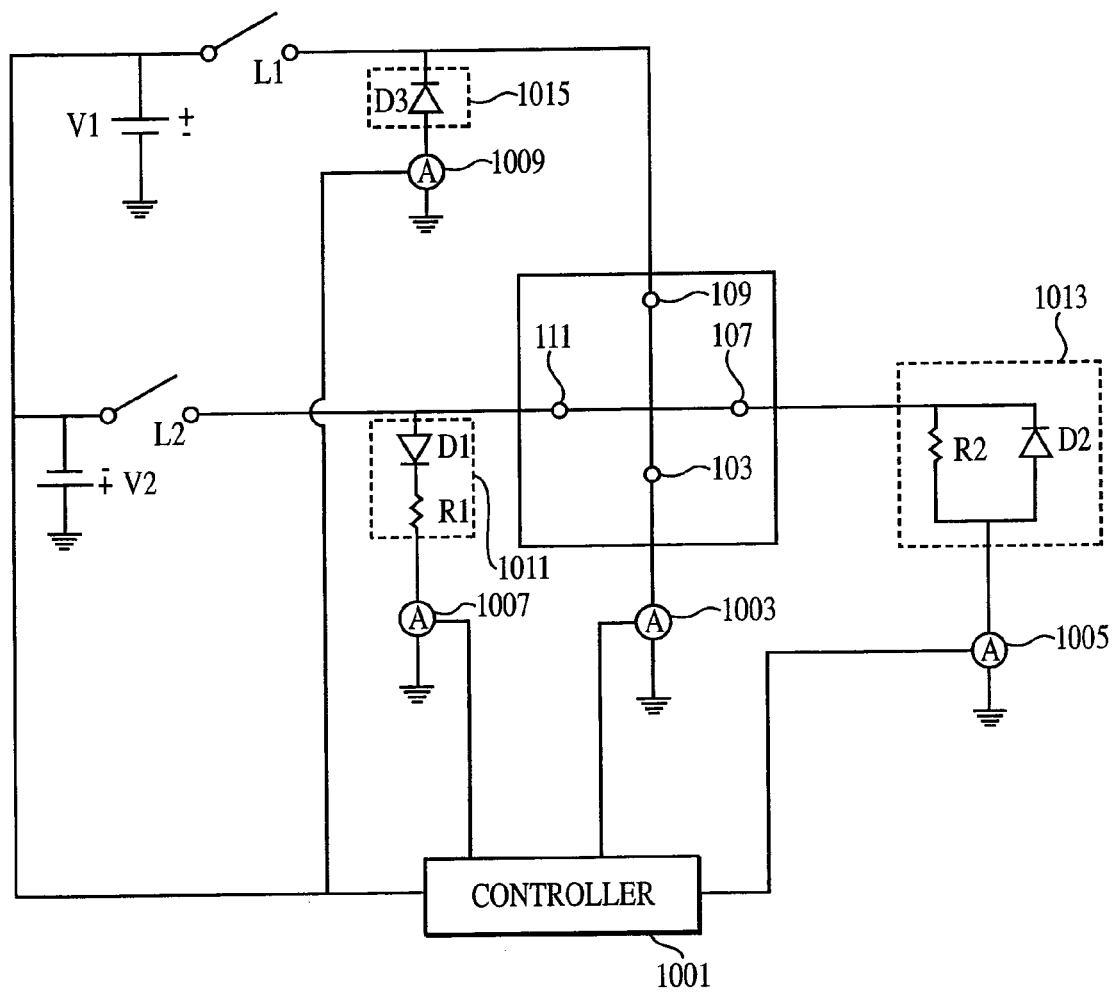
FIG. 7 shows one embodiment of an interface circuit connected to the balanced geometry CE microchip device.

FIG. 7 shows one embodiment of an interface circuit 1000 that may be connected to the balanced geometry CE microchip device 100. In one embodiment, interface circuit 1000 includes a controller 1001, a first voltage supply V1, a second voltage supply V2, a first switch L1, and a second switch L2.

The first switch L1 is preferably connected in series between the first voltage supply V1 and the buffer reservoir 109. Similarly, the second switch is preferably connected in series between the second voltage supply V2 and the waste reservoir 111. The controller 1001 is then coupled to the first switch L1 and the second switch L2 to control operation of the first and second switches.

As shown in FIG. 7, interface circuit 1000 may further include a first measuring circuit 1003 connected to the detection reservoir 103, a second measuring circuit 1005 connected to the sample reservoir 107, a third measuring circuit 1007 connected to the waste reservoir 111, and a fourth measuring circuit 1009 connected to the buffer reservoir 109. In one approach, the third measuring circuit 1007 may be connected to the waste reservoir 111 in parallel with the second switch L2. Similarly, the fourth measuring device 1009 may be connected to the buffer reservoir 109 in parallel with the first switch L1. The controller 1001 may then be coupled to each of the measuring circuits 1003, 1005, 1007, and 1009 to receive current measurements. In one embodiment, each of the measuring circuits 1003, 1005, 1007, and 1009 are an ammeter.

Interface circuit 1000 may also include a first current limiting circuit 1011 connected in series between the third measuring circuit 1007 and the waste reservoir 111, a second current limiting circuit connected 1013 in series between the second measuring circuit 1005 and the sample reservoir 107, and a third current measuring 1015 circuit connected in series between the fourth current measuring circuit 1009 and the buffer reservoir 109. In one embodiment, the first current limiting circuit is a resistor R1 connected in parallel with a diode D1, the second current limiting circuit is a resistor R2 connected in series with a diode D2, and the third current limiting circuit is a diode D3.

Figure 8:
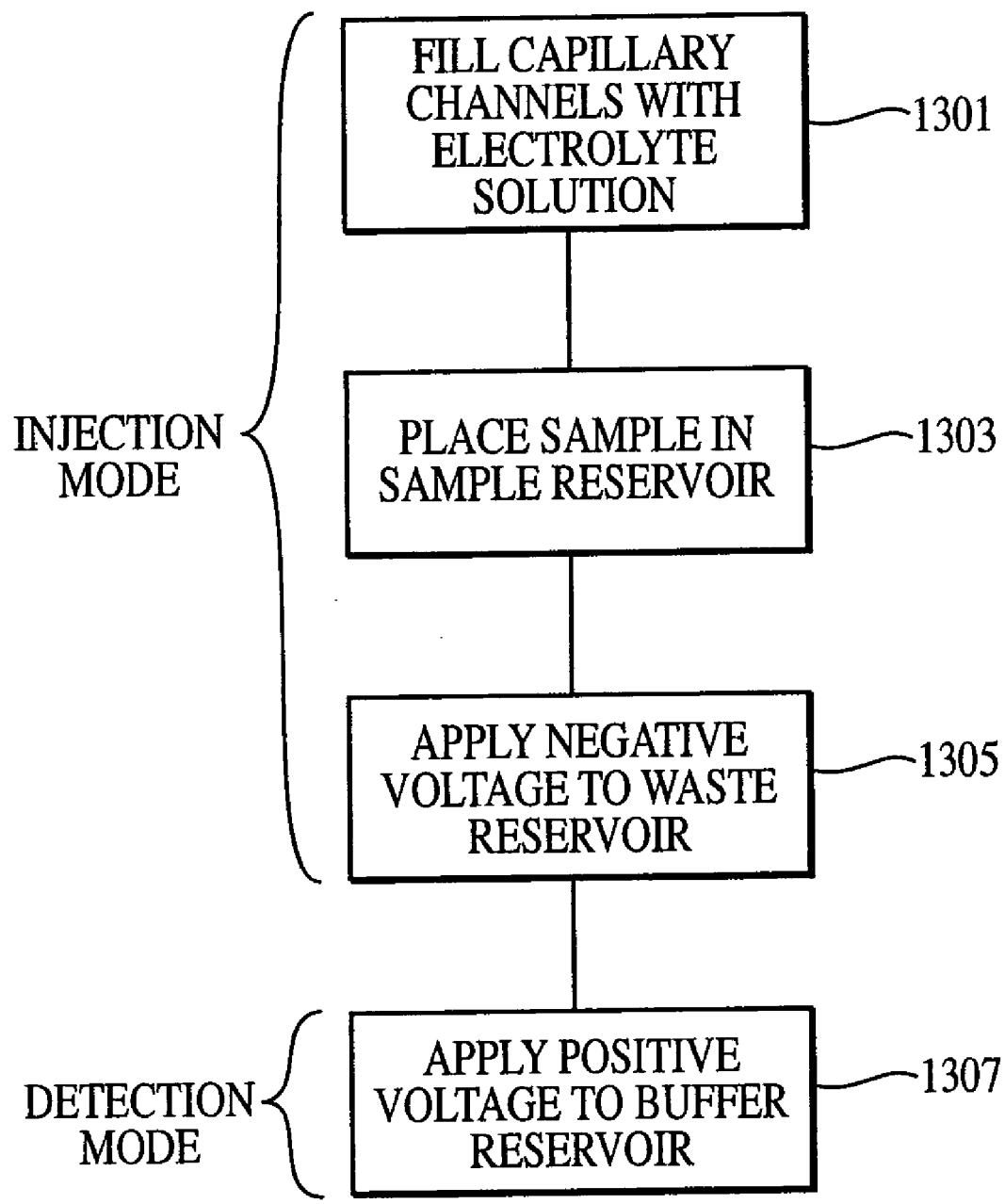
FIG. 8 is a flow chart illustrating the utilization of the interface circuit connected to the balanced geometry CE microchip device.

FIG. 8 is a flow chart illustrating the utilization of the interface circuit 1000 connected to the balance geometry of the CE microchip device 100. In step 1301, the capillary channels 113, and 115 are filled with an electrolyte solution. In step 1303, a sample of a substance is placed in the sample reservoir 107. In step 1305, a negative voltage is applied to the waste reservoir 111. The negative voltage is applied by opening, or turning OFF, the first switch L1 and closing, or turning ON, the second switch L2. In this configuration, the detection reservoir 103 is connected to ground through first measuring circuit 1003. In addition, diodes D3 and D1 are forward biased and act as short circuits to connect the buffer reservoir 109 and the sample reservoir 107 to ground through the fourth measuring circuit 1009 and the second measuring circuit 1005, respectively. Diode D2 is reversed biased and acts as an open circuit. Under these bias conditions, the electrolyte solution flows from the buffer reservoir 109, sample reservoir 107 and detection reservoir 103 to the waste reservoir 111, forming a pinched and stable volume plug. Steps 301, 303, and 305 may collectively be referred to as the injection mode.

By utilizing the balanced geometry CE microchip device described above, the system remains balanced even if the properties of the electrolyte solution change. More specifically, a change in the buffer concentration as well as pH will change only the speed of the flow of the solution, not the direction of the flow. A lower pH (more acidic) and lower concentration make the fluid flow slower, while a higher pH (more basic) and higher concentration make the fluid flow faster. An analyte is always at a low concentration; thus it is assumed that presence of the analyte will not affect the properties of the buffer solution.

After an analyte plug has formed at the capillary intersection, the CE chip is placed into the detection mode where the analyte plug moves into the detection capillary for separation and eventual detection. In the detection mode, the first switch L1 and the second switch L2 are toggled such that the first switch is now closed and the second switch is open. As a result, a positive voltage is applied to the buffer reservoir 109. The positive voltage applied to the buffer reservoir 109 will be in the range to cause sufficient field strength in the detection capillary required for CE. For example, in one embodiment, the positive voltage may range from 0 to 1000V. In this configuration, the detection reservoir 103 remains connected to ground through measurement circuit 1003, diodes D3 and D1 are reverse biased and act as an open circuit, diode D2 is forward biased and connects the waste reservoir 111 through resistor R2 and the third measuring circuit 1007 to ground, and the sample reservoir 107 is connected through resistor R1 and measurement circuit 1005 to ground. Under these conditions, the electrolyte solution flows from buffer reservoir 109 to the detection reservoir 103 to the waste reservoir 111 and sample reservoir 107. The analyte plug moves towards the detection reservoir 103, whereby the solution can be measured and analyzed. The flow rates to the waste reservoir 111 and sample reservoir 107 are in part determined by resistors R1 and R2.

The forward biased and reversed biased functions of the diodes used in the interface circuit may also be accomplished using other devices including switches, relays, as well as other semiconductor devices.

Figure 9A:
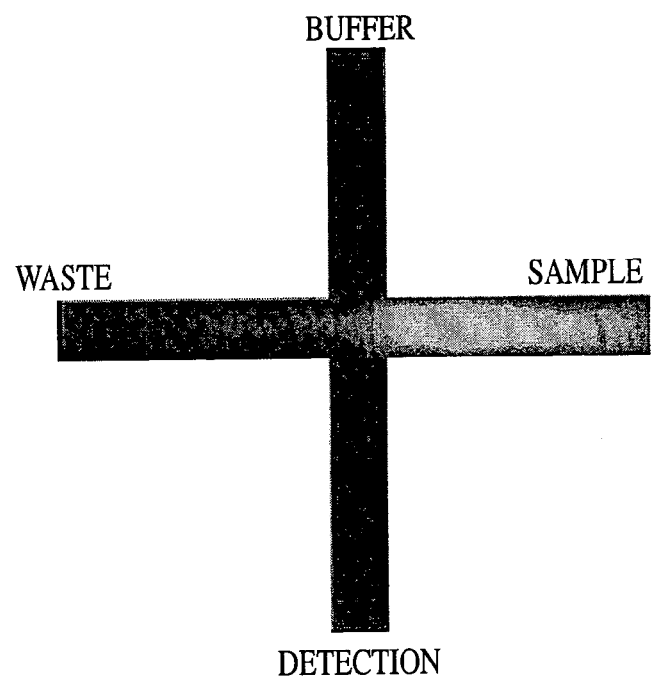
FIGS. 9A and 9B are images of injection and detection modes of the balanced geometry CE microchip device.
Figure 9B:
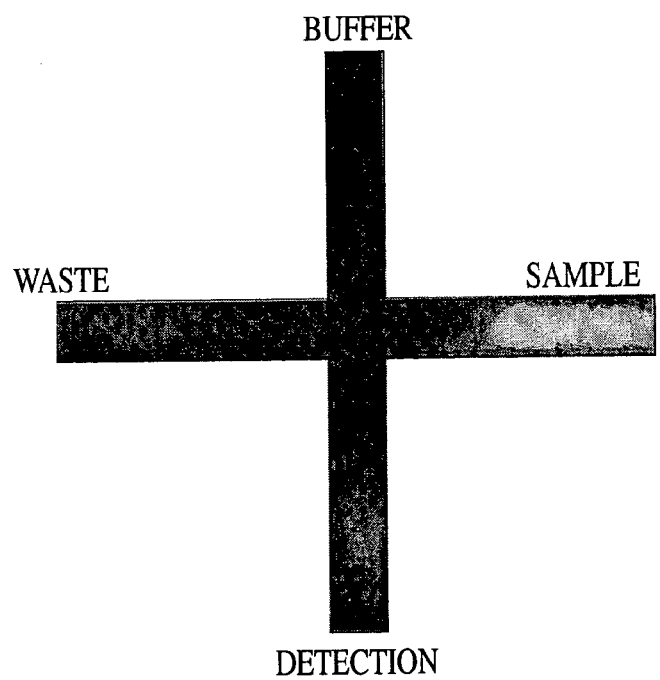

FIGS. 9A and 9B are images of injection and detection modes, respectively, of the balanced geometry CE microchip device 100. Specifically, in FIG. 9A, a sample substance is shown flowing from sample reservoir 107 to the waste reservoir 113 during the injection mode. In addition, the buffer solution is also flowing from the detection reservoir 103 and buffer reservoir 111 to the waste reservoir 113. The effect of the sample substance flowing from the buffer reservoir 111 is shown by the substance flow pinching at an intersection of the capillary channels 113 and 115 and the dilute concentration in capillary 113 close to the waste reservoir 113.

In FIG. 9B, there is an image of the detection mode of the balanced geometry CE microchip device 100. In this detection mode, the buffer solution is shown traveling from the buffer reservoir 111 toward the detection reservoir 103, waste reservoir 113 and the sample reservoir 107. The analyte sample plug travels from the capillary intersection through the detection capillary for separation to the detection reservoir 103 for detection.

Figure 10:
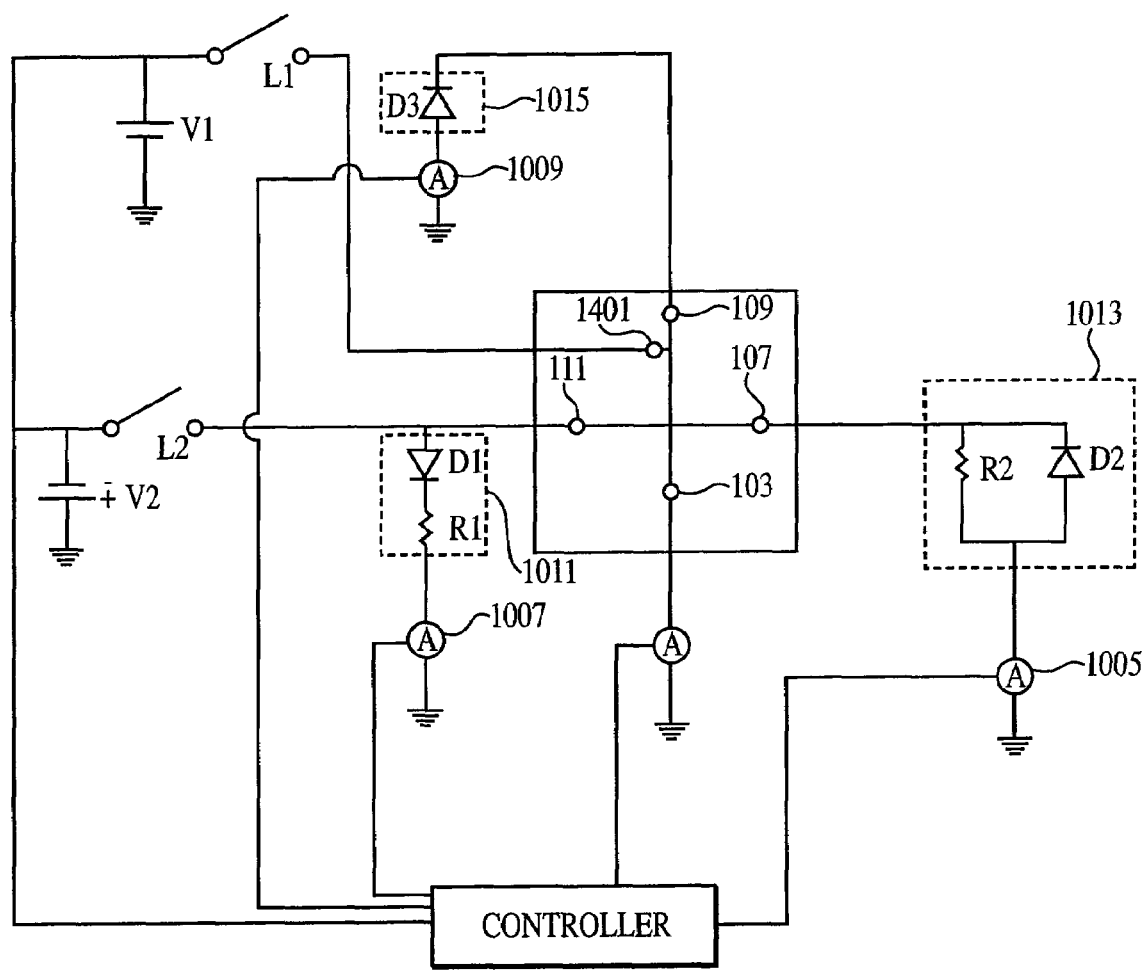
FIG. 10 shows an interface circuit connected to another embodiment of a balanced geometry CE microchip device.

FIG. 10 shows another embodiment of a balanced geometry CE microchip device 100 and the interface circuit 200. In this embodiment, in addition to the sample reservoir, the buffer reservoir, the waste reservoir, and the detection reservoir discussed above, the CE microchip device may also include a voltage receiving reservoir 1401 to reduce voltage loss near the intersection of the capillary channels 113 and 115. Accordingly, the voltage receiving reservoir is preferably in fluid communication with capillary channel 115 between the buffer reservoir 109 and the intersection of the capillary channels 113 and 115 via fluid channel 1403.

In one approach, the voltage receiving reservoir 1401 is positioned closer to the intersection of fluid channels 113 and 115 than sample reservoir 107 and waste reservoir 111. The distance between the voltage receiving reservoir 1401 and the buffer reservoir 109 may be in any range of distances such as half the distance from the intersection of the plurality of fluid channels 113 and 115 to buffer reservoir 109.

In this embodiment, the first switch L1 is connected in series with and between the first voltage supply V1 and the voltage receiving reservoir 1401, and the fourth current measuring circuit 1009 is connected to the buffer reservoir 109 in series with the third current limiting circuit 1015. The second voltage supply V2, the second switch L2, the first measuring circuit 1003, the second measuring circuit 1005, the third measuring circuit 1007, the first current limiting circuit 1011, and the second current limiting circuit 1013 are all connected in the same configuration as described above.

In operation, as in the embodiment described above, the capillary channels 113, 115, and 1403 are filled with an electrolyte solution and a sample of a substance (analyte) is placed in the sample reservoir 107. A negative voltage is then applied to the waste reservoir 111 by opening, or turning OFF, the first switch L1 and closing, or turning ON, the second switch L2. The electrolyte solution then flows to the waste reservoir 111, forming a pinched and stable volume plug.

The detection mode is then initialized and the first switch L1 and the second switch L2 are toggled such that a positive voltage is applied to the voltage receiving reservoir 1401. The electrolyte solution then flows from receiving reservoir 1401 to the detection reservoir 103 to the waste reservoir 111 and sample reservoir 107 as a plug, whereby the solution can be analyzed and calculated at detection reservoir 103. As the voltage receiving reservoir is closer to the intersection of the capillary channels 113 and 115 than the buffer reservoir, the voltage at the intersection of capillary channels is thus higher as compared to the voltage at the intersection when a voltage is applied to the buffer reservoir.

In another embodiment, the interface circuit may also be used to operate a parallel array of CE microchip devices from a single power supply, thus further reducing costs and increasing portability. For example, a single power supply (described below) may be connected to a plurality of CE microchip devices, each having different configurations, or using different electrode, materials.

Power Supply

Figure 11:
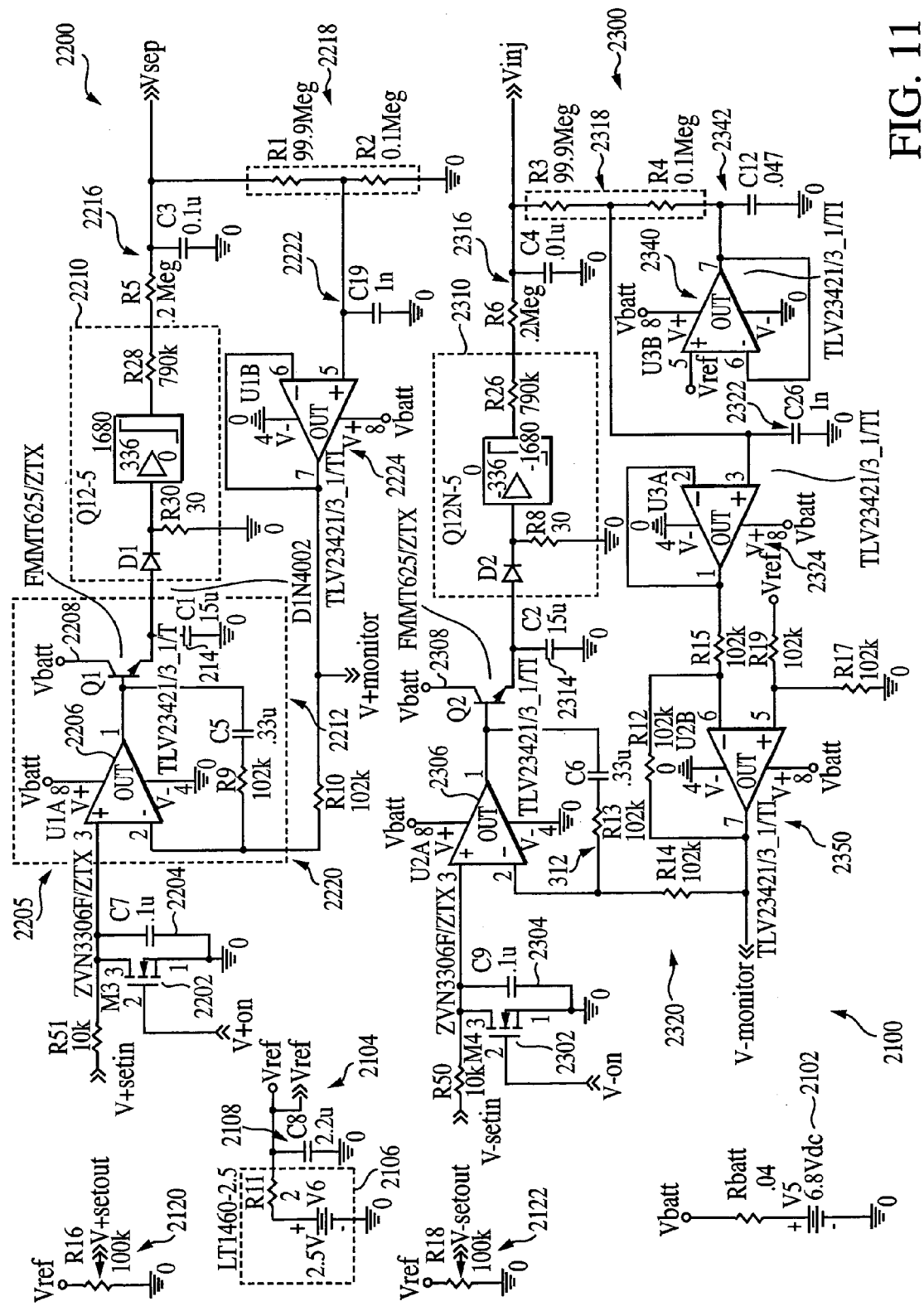
FIG. 11 is an electrical schematic diagram of one embodiment of a power supply.

In one embodiment, the CE microchip device may also be connected to a compact battery powered high voltage power supply. FIG. 11 shows one embodiment of a high voltage power supply that is substantially smaller and lighter than conventional benchtop high voltage power supplies. In one embodiment, the power supply may be operated on 4 "AA" batteries or an external DC source.

The high voltage power supply 2100 preferably has two sources, a positive voltage source 2200 that supplies the positive voltage for the first voltage source V1 in the interface circuit and a negative voltage source 2300 that supplies a negative voltage for the second voltage source V2 in the interface circuit. A reference voltage circuit 2104 is used to supply a reference voltage for each of the positive and negative high voltage sources 2200 and 2300. The reference voltage circuit 2104 may include a dc voltage source with intrinsic output resistance. One example of such a reference voltage circuit is LT1460-2.5 model 106 from Linear Technology. A lowpass filter 108, preferably comprised of a capacitor C8, is then connected in parallel with the output of the reference voltage circuit 2104 to reduce noise from the reference voltage circuit 2104, Set voltages, which are output from voltage selectors 2120 and 2122, are selected as input voltages to be converted to high voltages for the positive voltage source 2200 and a negative voltage source 2300, respectively. In one embodiment, each voltage selector 2120 and 2122 contains a potentiometer connected between the reference voltage and ground. The positive set voltage from voltage selector 2120 is supplied to the positive voltage source 2200 and the negative set voltage from voltage selector 2122 is supplied to the negative voltage source 2300.

The positive voltage source 2200 and the negative voltage source 2300 each include a DC-DC converter 2210 and 2310, respectively, for converting an input voltage into a high output voltage. As previously described, during the injection mode, a negative voltage of hundreds of volts may be supplied to the waste reservoir, and during the separation-detection mode, a positive voltage of hundreds of volts may be supplied to the CE reservoir. Thus, a low noise DC-DC converter 2210, 2310 is necessary to boost the supplied voltage from a few volts to several hundred volts.

In one embodiment, the DC-DC converters 2210 and 2310 are model Q12-5 and Q12-5N EMCO® High Voltage Corp. Q series DC-DC converters. These modules are rated to supply up to +1.2 kVDC and −1.2 kVDC at 400 µA, giving an output range of about +200V to about +1 kV and about −200V to about −1 kV, respectively. These DC-DC converters also contain a quasi-sinusoid oscillator, step-up transformer and rectifier. As a result the converters are low power (0.5 W), and produce low output ripple and EMI. The input range of the converters 0.7 to 5 VDC and the size of each converter is only 0.125 cubic inches (50 cubic cm). Of course, other DC-DC converters may also be used.

The positive voltage source 2200 and the negative voltage source 2300 each include a closed loop regulation circuit 2220 and 2320, respectively, to compensate for varying loads and battery discharge, as well as to adjust the output voltage. The regulation circuits 2220 and 2320 also regulate and decreases an output impedance of the DC-DC converters. The input to the regulation circuits 2220 is the positive set voltage supplied to a control circuit 2202, and the input to the regulation circuit 2320 is the negative voltage supplied to a control circuit 2302. The control circuits 2202 and 2302 control transfer of the set voltage to the remainder of the circuit, for example, by turning the circuit on/off in response to a computer control. The control circuits 2202 and 2302 may include an enhancement-mode n-channel MOSFET 2002 having a gate connected with a control voltage, a source connected with ground, and a drain connected with the set voltage through a resistor. Low pass filters 2204 and 2304 may then be connected in parallel with control circuits 2202 and 2302, respectively, to reduce the high frequency noise components. In one approach, low pass filters 2024 and 2304 are 0.1 uF capacitors C7 and C9.

The closed loop regulation circuit 2220 in the positive voltage source includes an error amplifier buffer 2206, a drive transistor 208, the DC-DC converter 2210 described above, and a buffer 2224. The error amplifier 2205 compares a control voltage with an output feedback signal from buffer 2224 and adjusts an output to correct the error. In one approach, the error amplifier may be an op amp 2206 whose power terminals are connected with the battery voltage and ground, thus using a single rail supply that in one embodiment is a positive voltage of 6.8 Vdc supplied by 4 "AA" batteries. The positive input terminal of the op amp 2206 is supplied with the set voltage received from the output of control circuit 2202. The output of the op amp is fed back to the negative input terminal of the op amp through a feedback circuit 2212. In one approach, this feedback circuit 2212 may contain an RC series combination of a 102 k resistor R9 and a 0.33 uF capacitor C5. It is noted that if an op amp having a shut down control is substituted for the input buffer 206, the MOSFET 2202,2302 may be removed.

The output of the error amplifier 2206 is then connected with the input of the driver transistor 2208. The driver transistor 2208 buffers the output signal of the op amp 2206 and drives the input of the DC-DC converter 2210. In one approach, the drive transistor 2208 may be an emitter-follower n-p-n bipolar junction transistor having a base connected with the output of the error amplifier 2206, a collector connected with the battery supply, and an output taken from the emitter. The combination of the error amplifier 2206 and drive transistor 2208 acts as the regulator that compares the feedback signal to the reference signal. The output of drive transistor 2208 is then supplied to the DC-DC converter 2210. Another low pass filter 2214 may be disposed between the drive transistor 2208 and the DC-DC converter 2210. In one approach, this low pass filter 2214 may be a 15 uF capacitor connected between ground and the connection between the output of the unity gain buffer 2208 and the input of the DC-DC converter 2210.

The output voltage of the DC-DC converter 2210 is supplied to an external RC filter 2216 to reduce ripple of the output voltage. In one approach, the external RC filter 2216 includes a 0.2 Meg resistor R5 in series with the output of the DC-DC converter 2210 and a 0.01 uF capacitor C3 connected to ground. The output of this external RC filter 2216 is supplied as the CE detection mode voltage positive for first the voltage supply V1 in the interface circuit.

The output of the positive voltage source 2200 is also fed back to the negative input terminal of the input buffer 2206 to regulate the output of the high voltage source 2200. However, the output voltage needs to be decreased to enable it to be fed back to elements in the positive voltage source feedback loop. Specifically, the voltage needs to be decreases such that the voltage supplied to the feedback loop is between the battery voltage and ground. In one approach, the voltage should be reduced by a factor approximately equal to the factor by which the set voltage to the positive power source was increased to generate the output voltage. Alternatively, the voltage may be reduced by a large set amount, such as 1000, to maintain the voltage below that of the battery voltage.

Accordingly, the output of the positive voltage source 2200 may be supplied to a voltage reduction circuit 2218. As shown, the voltage reduction circuit 2218 may simply be a voltage divider that is comprised of a resistor R3 and a resistor R4 and that has a voltage reduction of the maximum amount necessary, in this case, 1000×. The output of the voltage divider 2218 is the node between the two resistors R1 and R2.

The divided voltage from the node between the resistances of the voltage divider 2218 is supplied to a buffer 2224. Capacitor 2222 serves to compensate for the high capacitance of the high resistance section of 2218 preventing voltage spikes from appearing at the input to buffer 2224. The buffer 2224 may be a voltage follower op amp with the divided voltage supplied to the positive input terminal and the output and negative input terminal directly connected together. This enables the buffered divided voltage to be monitored by an external monitor 2400 without loading down the divided voltage. A resistor may then be connected between the terminal leading to the external monitor 2400 and the negative input terminal of the input buffer 2206.

Similar to the positive voltage source 2200, the closed loop regulation circuit 2320 in the negative voltage source 2300 may also includes an error amplifier 2306, a driver transistor 2308, and a DC-DC converter 2310 connected in the same configuration as in the positive voltage source 2200. Specifically, error amplifier 2306 may be an op amp whose power terminals are connected with the battery voltage and ground. The positive input terminal of the op amp is supplied with the set voltage received from the output of control circuit 2302. The output of the op amp is fed back to the negative input terminal of the op amp through a feedback circuit 2312, which may be comprised of an RC series combination of a 102 k resistor R13 and a 0.33 uF capacitor C6.

The output of the error amplifier 2306 is connected with the input of the driver transistor 2308. The output of the driver transistor 2308 is then supplied to the DC-DC converter 2310. A low pass filter 2314 comprised of a 15 uF capacitor C2 may also be disposed between the driver transistor 2308 and the DC-DC converter 2310.

The set voltage is supplied to the input of the DC-DC converter 2310 and the output voltage from the DC-DC converter 2310 is supplied to an external RC filter 2316 to reduce ripple of the output voltage. In one approach, the external RC filter 2316 includes a 0.2Meg resistor R6 in series with the output of the DC-DC converter 2310 and a 0.01 uF capacitor C4 connected to ground. The output of this external RC filter 2316 is supplied as the CE injection mode voltage for second voltage supply V2.

The output of the negative voltage source 2300 is also fed back supplied to a voltage reduction circuit 2318. As shown, the voltage reduction circuit 2318 may be a voltage divider comprised of a resistor R3 and a resistor R4. The output of the voltage divider 218 is the node between the two resistors R3 and R4.

The negative high voltage source 2300 also includes an offset circuit 2340 in the negative source feedback loop that allows the negative high voltage source 2300 to operate from the single rail supply. Thus, while the base of the voltage divider 2218 in the positive voltage source 2200 is connected with ground, the base of the voltage divider 2318 of the negative high voltage source 2300 is connected with an offset voltage to allow a positive voltage to be fed into the op amps in the feedback loop (which are themselves powered by a single positive source). In one embodiment, the offset circuit 2340 may be a voltage follower op amp whose input to the positive terminal is the reference voltage and whose input to the negative terminal is a direct feedback from the output of the follower op amp. The output of the voltage follower op amp is thus the reference voltage, but the reference voltage is buffered so that the reference voltage may be used without loading down the reference voltage. The output of the voltage follower is supplied to a node between a low pass filter 2342 of a capacitor C12 connected to ground and the base of the voltage divider. Accordingly, the offset voltage is the reference voltage, i.e. about 2.5 volts.

The divided voltage from the node between the resistances of the voltage divider 2318 is supplied to a buffer 2324 through another low pass filter 2322. The buffer 2324 is similar in configuration to buffer 2224 in the positive voltage source 2200. As such, buffer 2324 may be a voltage follower op amp with the divided voltage supplied to the positive input terminal and the output and negative input terminal directly connected together.

The buffered divided voltage output from the internal buffer 2324 is hen supplied to a subtractor 2350 that removes the offset before supplying the buffered divided voltage to the external monitor 400 and feeding the buffered divided voltage back to the negative input of the error amplifer 2306. The subtractor 2350 may be an op amp having the buffered divided voltage supplied to the negative input terminal through a resistor R15. The negative input terminal is connected with the output terminal through a resistor R12 having the same value as the resistor R15. The offset voltage (in this case the reference voltage) is divided in half by a voltage divider circuit having the same resistances as the resistors R12 and R15 and the half voltage is supplied to the positive input terminal of the subtractor op amp 2350. The output of the subtractor op amp 2350 is then supplied to the external monitor 2400 and the negative input terminal of the input buffer 2306 of the negative voltage supply 2300.

By using the high voltage power supply shown in FIG. 11 the weight of the voltage power supply for a CE microchip device is reduced by a factor of about 40, from about 20 lbs in conventional power supplies to about 0.5 lb (0.23 kg). The size of the device is also reduced by a factor of about 200, from about 24"×18"×6" (610 cm×46 cm×15 cm) in conventional power supplies to about 3"×4"×1" (7.5 cm×10 cm×2.5 cm). This permits the present high voltage power supply to be incorporated into a hand-held lab-on-a-chip type device. In addition, the present high voltage power supply costs substantially less than the typical bench top voltage supply. For example, the present miniature high voltage supply costs about $500 as compared with the typical bench top voltage supply costing about $2000. The present voltage supply may also include other advantages, such output ripple of less than 10 mV peak-to-peak at a load of 2.5 MΩ and 1 kVDC, an accuracy of <0.36%, an operating time of 15 hours at a load of 10 MΩ and 30 hours at a load of 100 MΩ, stored energy of <60 mJ per source and steady state regulation of <0.1% from a load of 2.5 MΩ to 100 MΩ.

Although the device, as shown has no on-board current monitoring circuit, input voltage protection or AC mains capacity, which are well known in the art, may be included to provide these functions without substantially increasing the cost, size or weight. Similarly, indicators such as meters and LEDs (means for indicating the output voltage) may be added without changing the basic core of the present system. Of course, although in the arrangement shown a single rail system is used to supply power to the various elements, a dual rail system may also be used. For example, rather than having the op amps powered by the battery and ground, the op amps in the power supply may be powered by both positive and negative voltages.

Additionally, the DC-DC converters 2210 and 2310, as well as any other components in the voltage sources 2200 and 2300 may be modular. Thus, the components may be mounted in a socket rather than soldered onto the PCB, and as a result, may be swapped within a single circuit design.

Detection Circuit

Conventional amperometric detection circuits use three electrodes for detection of the sample. The three detection electrodes include a counter electrode (also referred to as an auxiliary electrode), a reference electrode, and a work electrode. The work electrode detects the oxidation or reduction current taking place due to the voltage potential between the work electrode and the solution surrounding the work electrode. The voltage potential is referred to as the "work electrode applied potential" or "Vapp". The work electrode applied potential is established by a control circuit (referred to as a potentiostat) driving the auxiliary electrode and controlled by the reference electrode.

When amperometric detection is combined with the capillary electrophoresis technique of separation, the detection electrodes are often placed at the end of the capillary. Since an electrical current must flow through the capillary for electrophoresis to take place, a CE electrode is also placed near the end of the capillary resulting in a total of four electrodes at the detection end of the capillary. The CE voltage source and detection circuits are typically isolated by using transformers or other isolation techniques included optical coupling. Isolation complicates circuit and overall instrument design.

The present invention includes a three electrode design in which the auxiliary electrode also functions as the CE electrode. This three electrode configuration uses no isolation between the detection and CE circuits allowing the circuits to share a common ground resulting in a simple circuit design with fewer components and with low power requirements.

Figure 12:
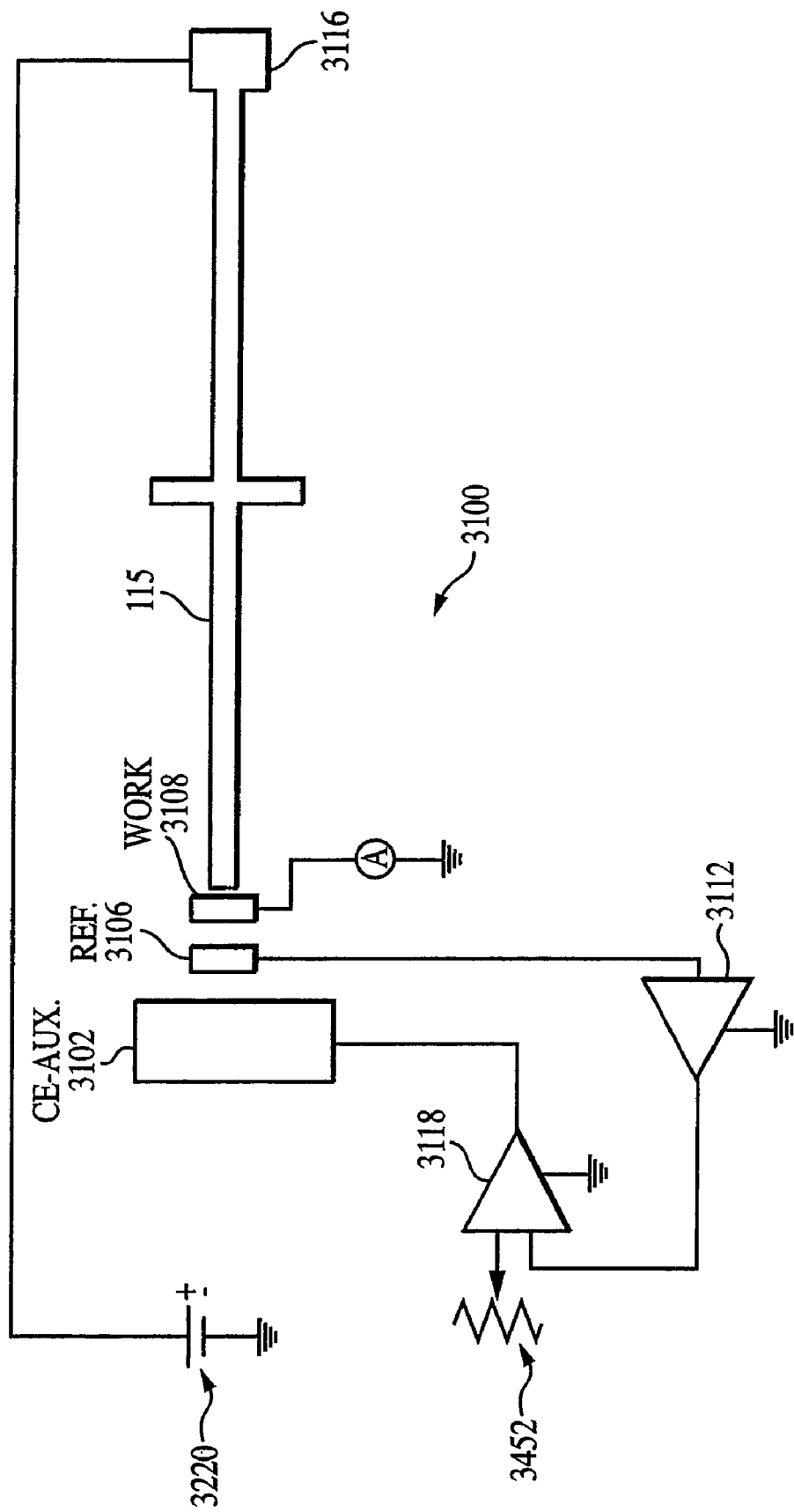
FIG. 12 shows one embodiment of an electrode configuration associated with a balanced geometry CE microchip device.

FIG. 12 illustrates an electrode configuration 3100 in which a single CE-Aux electrode 3102 acts as both the auxiliary electrode and CE cathode. In one embodiment, the work electrode 3108 (also shown as electrode 121b in FIG. 4A) is disposed close to the separation capillary 115 and the reference electrode 3106 (also shown as electrode 121a in FIG. 4A) is placed near the work electrode 3108 so that the potential of the solution surrounding the work electrode 3108 can be accurately determined. The combination CE-auxiliary electrode 3102 is positioned away from the work and reference electrodes at a distance typically greater that the distance of the work to reference electrode separation.

To prevent the reference electrode 3106 from influencing the solution potential and to prevent electrochemistry reactions caused by the reference electrode, the reference electrode is also connected to the input of the potentiostat circuit 3452 through a high impedance buffer amplifier. In one embodiment, the reference electrode 3106 may be connected to a high impedance op amp 3112 whose output is connected to a second op amp 3118. The output of the second op amp 3118 is then connected with the CE-Aux electrode 3102 and provides the voltage for the CE-Aux electrode 3102 from a reference input.

For a positive electrochemical detection potential (Vapp), the CE-Aux electrode 3102 is pulled below ground potential to a voltage where the electrolyte solution is Vapp volts (for example, about 1.5V) below the work electrode 3108, thus resulting in a positive work-to-reference-electrode-potential. As the present detection scheme shown in FIG. 12 uses end-column placement of the detection electrodes, the voltage potential difference between the work electrode and CE-Aux electrode is very low and requires only a low voltage source to power the circuit.

Figure 13:
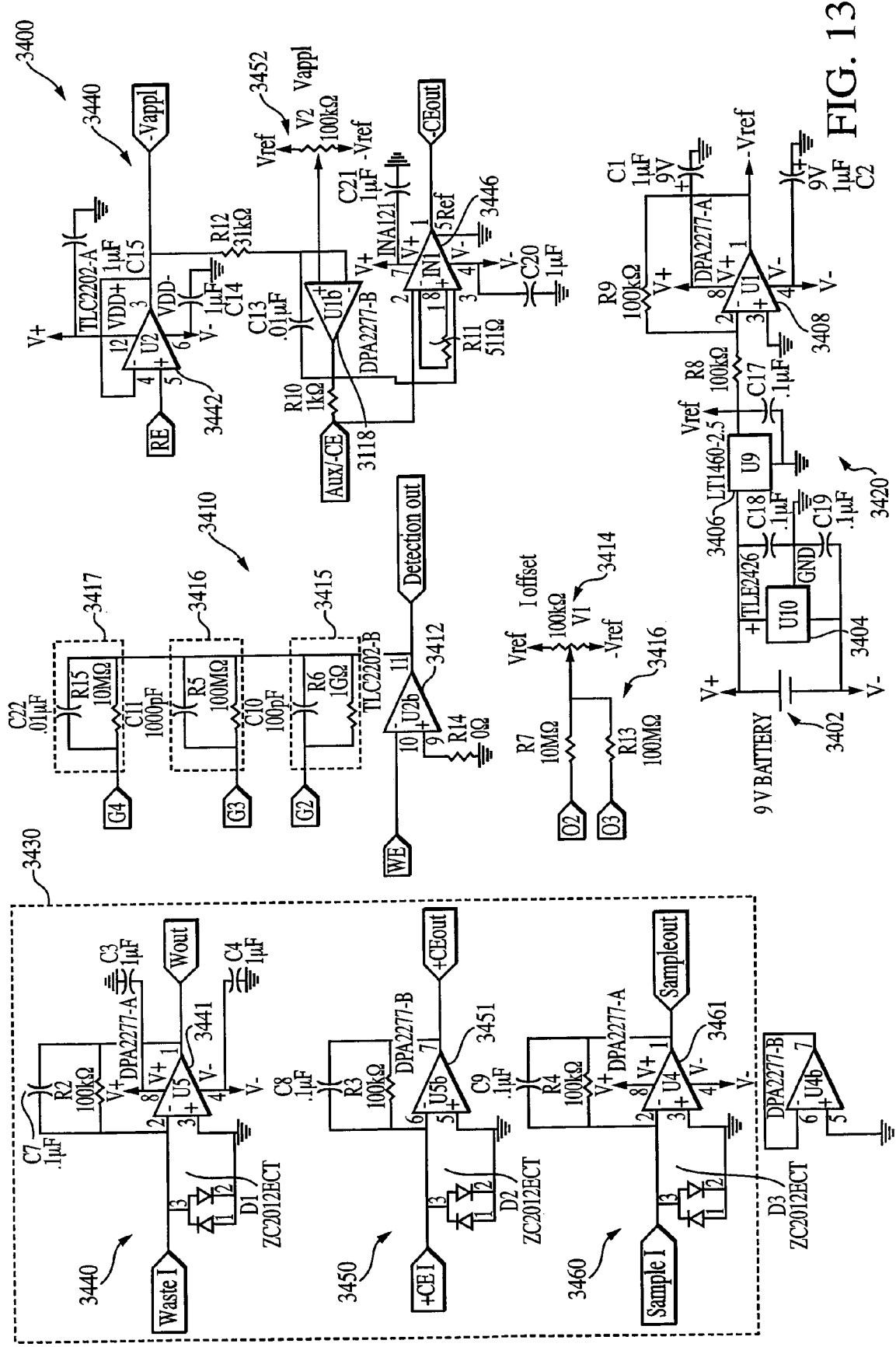
FIG. 13 shows an electrical schematic of a detection circuit according to the first embodiment.

One embodiment of a detection circuit is illustrated in FIG. 13. The detection circuit 400 uses a battery 3402 to supply power to the various op amps of the circuit. In one embodiment, the battery is a 9V battery. A reference circuit 3420 includes a virtual ground circuit 3404, a reference integrated circuit 3406, and an inverting reference buffer 3408. As shown in FIG. 13, the inverting reference buffer 3408 may be an op amp.

The reference circuit 3420 converts the battery 3402 to a source of both positive and negative voltage. The reference integrated circuit 3406 and reference buffer 3408 provide a positive and negative reference voltage, respectively, to the remainder of the circuit 3400. The output of the reference integrated circuit 3406 is connected with the negative input terminal of the reference buffer 3408 through a resistor R8. The output of the reference buffer 3408 is then connected to the negative input terminal through a resistor R9 preferably having the same value as resistor R8. The positive input terminal of the reference buffer 3408 is connected with ground.

A capillary current monitor circuit 3430 has three buffers 3440, 3450, and 3460 that monitor currents in the waste, CE, and sample capillaries, respectively. In one embodiment, the three buffers may be op amps with each having a substantially similar configuration. More specifically, the waste buffer 3440 includes an op amp 3441 having a positive input terminal connected to ground and a negative input terminal connected to an electrode 3444 in or near the waste reservoir. The op amp further includes an output terminal 3445 connected with the negative input terminal 3443 through a parallel RC circuit 3446. Similarly, the CE buffer 3450 includes an op amp 3451 having a positive input terminal connected to ground, a negative input terminal connected to an electrode 3454 in the buffer reservoir, and an output terminal connected with the negative input terminal through a parallel RC circuit 3456. The sample buffer 3460 includes an op amp 3461 having a positive input terminal connected to ground, a negative input terminal connected to an electrode 3464 in the sample reservoir, and an output terminal connected with the negative input terminal through a parallel RC circuit 3466.

A current-to-voltage detector 3410 is configured using a single op amp 3412. The positive input terminal is grounded and the negative input terminal is connected with work electrode 3108. The current from the work electrode 3108 is also fed to the output of the detector op amp 3412 through one of several parallel RC circuits 3415, 3416, and 3417. The gain of the current-to-voltage detector 3410 is controlled by the particular resistance value selected since the voltage produced at the output of the detector is, of course, merely the current detected multiplied by this resistance. In one embodiment, the selectable resistances vary from 10 MΩ to 1 GΩ, leading to a sensitivity of between 1 nA/V and 100 nA/V (i.e. for 10 MΩ, 100 MΩ and 1 GΩ resistors, the sensitivities are 100 nA/V, 10 nA/V and 1 nA/V). Of course, the gain ranges here are merely exemplary as gain may be simply a function of the feedback resistor for which there is a wide range of values.

Additionally, the frequency response of the current-to-voltage detector 3410 is at least in part determined by the capacitor in parallel with the resistor. A long RC time constant will reduce the noise while increasing the gain, but a short time constant improves the response time of the detector. Thus, whether a short or long time constant is used may depend on the particular application of the device.

Current offset correction for the current detector 3410 is provided by a current offset circuit 3414, which in one example is a potentiometer. The potentiometer is connected between the positive and negative reference voltages provided by the reference circuit 3420. The output of the potentiometer 3414 is connected with the negative input terminal of the detector op amp 3412 and thus the work electrode through a selectable resistor 3416.

The detector circuit 3400 also contains an electrode potential setting circuit 3440 that controls the relative potential of the work electrode 3106 and electrolyte solution in the detection reservoir. As shown in FIG. 12, as well as FIG. 13, the reference electrode 3108 is connected with the positive input terminal of a reference buffer 3442. The output of the reference buffer 3442 is connected with the negative input terminal of the reference buffer 3442 so that the output of the reference buffer 3442 is effectively the buffered value of the reference electrode 3108. The output of the reference buffer 3442 in the electrode potential setting circuit 2440 is also connected to the negative input terminal of a CE-Aux electrode buffer 3444 through a feed resistor R12.

The CE-Aux electrode buffer 3444 may also be an op amp whose positive input terminal is connected with an on-board control circuit 3452, which in one example is a potentiometer. The potentiometer 3452 is connected between the positive and negative reference voltages provided by the reference circuit 3420. The output of the potentiometer 3452 is connected with the positive input terminal of the CE-Aux electrode buffer 3444 to set the virtual potential of the negative input terminal of the CE-Aux electrode buffer 3444 and thus the potential of the electrolyte. The output of the CE-Aux electrode buffer 3444 is connected to the negative input terminal of the CE-Aux electrode buffer 3444 through a feedback capacitor 3454. The output of the CE-Aux electrode buffer 3444 is also connected to the CE-Aux electrode 3102 through a CE-Aux resistor 3456.

The output of the reference buffer 3442 may also connected with an external monitor (not shown) to allow monitoring and adjustment of the electrolyte in the detection reservoir via the potentiometer 3452. An instrument amplifier 3446, which may also be an op amp, is provided to monitor the current flowing through the CE-Aux resistor 3456 to the CE-Aux electrode 3102. The negative input of the instrument amplifier 3446 is connected to the CE-Aux electrode 3102 while the positive input of the instrument amplifier 3446 is connected to the CE-Aux electrode op amp 3444 and the output of the instrument amplifier 3446 is connected with another external monitor (not shown). The instrument amplifier 3446 may also be powered by the positive and negative reference voltages provided by the reference circuit 3420.

Other embodiments of the detection circuit may include additional filters or a differential input to the detector to improve performance. Similarly, potentiometric measurement capability may be added to form another embodiment of the detector.

Figure 14:
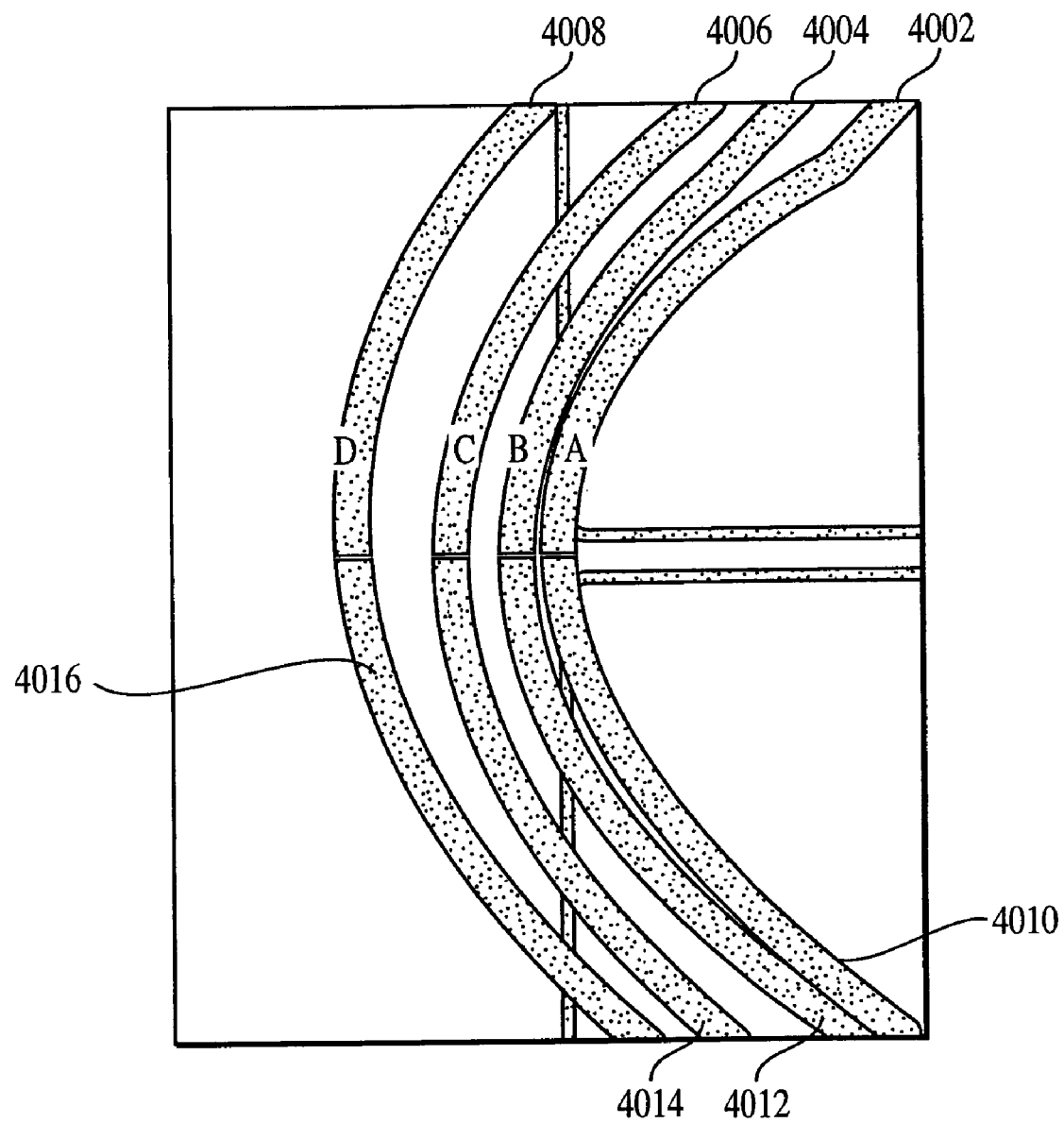
FIG. 14 shows another embodiment of an electrode configuration associated with a balanced geometry CE microchip device.

In another embodiment shown in FIG. 14, the CE microchip device 100 may also include a plurality of work electrodes and a plurality of reference electrodes. For example, as shown in FIG. 14, four work electrodes 4002, 4004, 4006, and 4008 and four reference electrodes 4010, 4012, 4014, and 4016 may be disposed in the detection reservoir. In one exemplary approach, the electrode widths are approximately 40 um, the spacing between the first pair of work/reference electrodes 4002, 4010 and the second pair of work/reference electrodes 4004, 4012 is approximately 10 um, the spacing between the second pair of work/reference electrodes 4006, 4012 and the third pair of work/reference electrodes 4008, 4014 is approximately 80 um, the spacing between the third pair of work/reference electrodes 4008, 4014 and the fourth pair of work/reference electrodes 4004, 4006 is approximately 150 um. Although each of the work electrodes is shown as being paired near an associated reference electrode, it should be understood that, depending on the application, the arrangement of work and reference electrodes may be altered.

This embodiment allows for the simultaneous investigation of analytes in a sample that may differ slightly in their particular method of detection. Specifically, devices with a single work electrode are inherently restricted to using an electrode composed of a single material, and are held at a particular operating voltage. By employing numerous work electrodes, detection of a sample may be conducted simultaneously using different work electrode materials and varying detection potentials. Positioning the electrodes at varying but specific locations may also allow for determination of optimum work electrode placement, as well as the effects of the high CE electric field on the quality of detection.

Additionally, one fundamental aspect to the utilization of ECD for quantitative determination of an analyte is the knowledge of the optimum applied potential for a particular analyte. Multiple working electrodes located near the exit of the separation capillary channel 115 may allow a user to obtain an hydrodynamic voltammogram in one analysis run. In addition, this multi-electrode configurations can be used to study future CE device configurations by allowing a user to hold specific experimental conditions constant and search for the optimal electrode design configuration.

While the invention has been described with reference to specific embodiments, the description is illustrative of the invention and not to be construed as limiting the invention. Various modifications and applications may occur to those skilled in the art without departing from the true spirit and scope of the invention as defined in the appended claims. For example, the apparatus may comprise different materials for the substrates and other components. Furthermore, all the dimensions of the device may be altered to accommodate different applications. Additionally, there are a variety of processes that can be used in all aspects of manufacturing to achieve similar results, such as those described in "Integrated Electrochemical Detection for Lab on a Chip Analytical Microsystems," Pai et al, (available on the Internet); and "Alternative Fabrication Methods for Capillary Electrophoretic Device Manufacturing," Conklin et al, (also available on the Internet). Accordingly, it is to be understood that the drawings and descriptions in this disclosure are proffered to facilitate comprehension of the invention and should not be construed to limit the scope thereof.

We claim:

1. A capillary electrophoresis device, comprising:
   (1) a substrate;
   (2) a first channel in the substrate, and having a buffer arm and a detection arm;
   (3) a second channel in the substrate intersecting the first channel, and having a sample arm and a waste arm;
   (4) a buffer reservoir in fluid communication with the buffer arm;
   (5) a waste reservoir in fluid communication with the waste arm;
   (6) a sample reservoir in fluid communication with the sample arm; and
   (7) a detection reservoir in fluid communication with the detection arm;
   wherein the detection arm and the buffer arm have a balanced flow rate upon application of a first voltage to the buffer reservoir, the detection reservoir, and the sample reservoir; and a second voltage to the waste reservoir.

2. The capillary electrophoresis device of claim 1 wherein the first voltage is ground.

3. The capillary electrophoresis device of claim 1 further comprising a voltage receiving reservoir in fluid communication with the buffer arm.

4. The capillary electrophoresis device of claim 1 further comprising three electrodes in the detection reservoir, at least two of said three electrodes are electrochemical detector electrodes.

5. The capillary electrophoresis device of claim 1 further comprising three electrodes in the detection reservoir.

6. The capillary electrophoresis device of claim 1 further comprising a CE-Aux electrode in the detection reservoir, wherein the CE-Aux electrode functions as both the auxiliary electrode for a detector and capillary electrophoresis cathode.

7. The capillary electrophoresis device of claim 1 further comprising a CE-Aux electrode in the detection reservoir, wherein the CE-Aux electrode functions as both the auxiliary electrode for a detector and capillary electrophoresis cathode.

8. The capillary electrophoresis device of claim 1 wherein the substrate is a first substrate, and further comprising a second substrate adjacent to and facing the first substrate, a shelf defined in the second substrate proximate to an outlet of the first channel and to the detection reservoir, the shelf configured to at least partially contain fluid in the detection reservoir.

9. The capillary electrophoresis device of claim 1 wherein the substrate is a first substrate, and further comprising
    at least one electrode in the detection reservoir;
    a second substrate facing the first substrate; and,
    a shelf defined in the second substrate proximate to an outlet of the first channel and to the detection reservoir, the shelf configured to at least partially contain fluid in the detection reservoir and in contact with the at least one electrode in the detection reservoir.

10. A method for performing capillary electrophoresis comprising the steps of:
    providing a substrate having:
      a first channel having a buffer arm and a detection arm;
      a second channel intersecting the first channel and having a sample arm and a waste arm;
      a sample reservoir for receiving a sample in fluid communication with the sample arm;
      a buffer reservoir in fluid communication with the buffer arm;
      a waste reservoir in fluid communication with the waste arm;
      a detection reservoir in fluid communication with the detection arm;
      wherein the first and second channels are filled with an electrolyte solution;
    applying a first voltage to the buffer, sample, and detection reservoirs and a second voltage to the waste reservoir to cause a balanced flow of the electrolyte solution from the buffer arm, the sample arm, and the detection arm towards the waste reservoir and to thereby form a pinched plug; and
    flowing the pinched plug along the detection arm to the detection reservoir.

11. The method of claim 10 wherein the substrate further has a voltage receiving reservoir in fluid communication with the buffer arm.

12. The method of claim 10 wherein the step of flowing the pinched plug along the detection arm to the detection reservoir comprises the steps of:
    using a first electrode in the detection reservoir to apply a potential to the detection reservoir and cause the pinched plug to flow towards the detection reservoir; and,
    using second and third electrodes in the detection reservoir to perform electrochemical analysis of the pinched plug.

13. A method for manufacturing a capillary electrophoresis device comprising:
    forming, in a first substrate:
    a first channel having a buffer arm and a detection arm;
    a second channel intersecting the first channel and having a sample arm and a waste arm;
    a sample reservoir for receiving a sample in fluid communication with the sample arm;
    a buffer reservoir in fluid communication with the buffer arm;
    a waste reservoir in fluid communication with the waste arm; and
    a detection reservoir in fluid communication with the detection arm;
    forming, in a second substrate:
    a waste reservoir electrode;
    a sample reservoir electrode;
    a buffer reservoir electrode; and
    at least three detection reservoir electrodes;
    aligning the first substrate with the second substrate; and
    bonding the first substrate to the second substrate,
    wherein forming a waste electrode, a sample electrode, a buffer electrode, and at least three detection electrodes comprises forming recesses in the second substrate and filling the recesses with conductive material.

14. The method of claim 13 wherein bonding the first substrate to the second substrate comprises applying pressure to the first and second substrates; and heating the first and second substrates.

15. The method of claim 13 wherein bonding the first substrate to the second substrate is carried out without applying an adhesive.

16. The method of claim 13 further comprising forming, in the first substrate, a voltage receiving reservoir in fluid communication with the buffer arm.

17. A capillary electrophoresis device, comprising:

(1) a capillary channel;

(2) a detection reservoir in fluid communication with the capillary channel;

(3) a CE-Aux electrode in the detection reservoir wherein the CE-Aux electrode functions as both the auxiliary electrode for a detector and capillary electrophoresis cathode;

(4) a reference electrode in the detection reservoir; and (5) a work electrode in the detection reservoir.

18. The capillary electrophoresis device of claim 17 and further comprising a shelf proximate to an outlet of the first channel and to the detection reservoir, the CE-Aux electrode, work electrode, and reference electrode at least partially positioned proximate to the shelf whereby the shelf at least partially contains fluid in the detection reservoir and in contact with the CE-Aux electrode, the work electrode, and the reference electrode.

* * * * *

UNITED STATES PATENT AND TRADEMARK OFFICE
CERTIFICATE OF CORRECTION

PATENT NO. : 7,344,628 B2  
APPLICATION NO. : 10/364658  
DATED : March 18, 2009  
INVENTOR(S) : Jackson et al.

Page 1 of 1

It is certified that error appears in the above-identified patent and that said Letters Patent is hereby corrected as shown below:

Title Page (Page 2):
OTHER PUBLICATIONS
    Second Col., First Line    Please delete "meccca" and insert --mecca-- in its place.

In the Specification:
    Col. 8, line 27    Please delete "C./" and insert --C/-- in its place.
    Col. 8, line 28    Please delete "C.," and insert --C,-- in its place.
    Col. 8, line 29    Please delete "C./" and insert --C/-- in its place.

Signed and Sealed this

Fifth Day of January, 2010

David J. Kappos
*Director of the United States Patent and Trademark Office*